(12) United States Patent
Charne et al.

(10) Patent No.: US 9,713,332 B2
(45) Date of Patent: Jul. 25, 2017

(54) **GLYPHOSATE APPLICATION FOR WEED CONTROL IN *BRASSICA***

(71) Applicant: PIONEER HI BRED INTERNATIONAL INC, Johnston, IA (US)

(72) Inventors: David George Charne, Guelph (CA); David Guevara, Milton (CA); Chadwick Bruce Koscielny, Miami (CA); Scott McClinchey, East Garafraxa (CA); Jayantilal Patel, Thornhill (CA); Lomas Tulsieram, Mississauga (CA)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 0 days.

(21) Appl. No.: 14/204,048

(22) Filed: Mar. 11, 2014

(65) Prior Publication Data

US 2014/0287922 A1    Sep. 25, 2014

Related U.S. Application Data

(60) Provisional application No. 61/779,347, filed on Mar. 13, 2013.

(51) Int. Cl.
*A01N 57/20* (2006.01)

(52) U.S. Cl.
CPC .................................. *A01N 57/20* (2013.01)

(58) Field of Classification Search
None
See application file for complete search history.

(56) References Cited

U.S. PATENT DOCUMENTS

| | | | |
|---|---|---|---|
| 8,575,431 B2 | 11/2013 | Charne et al. | |
| 8,581,046 B2 | 11/2013 | Charne et al. | |
| 8,816,156 B2 | 8/2014 | Brown et al. | |
| 8,993,238 B2 | 3/2015 | Charne et al. | |
| 2002/0006874 A1* | 1/2002 | Brigance et al. | 504/361 |
| 2003/0041357 A1* | 2/2003 | Jepson et al. | 800/300 |
| 2004/0082770 A1* | 4/2004 | Castle et al. | 536/23.2 |
| 2005/0223425 A1* | 10/2005 | Clinton et al. | 800/279 |
| 2011/0302667 A1* | 12/2011 | Brown et al. | 800/260 |
| 2012/0131690 A1 | 5/2012 | Charne et al. | |
| 2012/0131692 A1* | 5/2012 | Charne | A01H 5/10 800/267 |
| 2014/0099638 A1 | 4/2014 | Charne et al. | |
| 2014/0373190 A1 | 12/2014 | Brown et al. | |
| 2015/0119248 A1 | 4/2015 | Brown et al. | |

FOREIGN PATENT DOCUMENTS

WO    2012/071040 A1    5/2012

OTHER PUBLICATIONS

Duane R. Bergland et al., Canola Production A-686, Aug. 2007.
George W. Clayton et al., GlyphosateTiming and Tillage System Effects on Glyphosate-Resistant Canola (*Brassica napus*), Weed Technology, Jan. 31, 2002, pp. 124-130, vol. 16.
Steven G. Martin et al., Critical period of weed control in spring canola, Weed Science, May 31, 2001, pp. 326-333, vol. 49.
John Moore, Weed control strategies for glyphosate tolerant crops, May 17, 2010.
International Search Report—PCT/US2014/022908 Mailed Jul. 2, 2014.

* cited by examiner

*Primary Examiner* — Richard Schnizer
*Assistant Examiner* — Katherine Peebles

(57) ABSTRACT

The disclosure provides methods of applying glyphosate to improve weed control in a field containing herbicide tolerant *brassica* species. More specifically, glyphosate treatments are applied to a substantial portion of herbicide tolerant *brassica* plants which are beyond the 2-6 leaf stage such as for example to a substantial portion of herbicide tolerant *brassica* plants which are at the 10% open flowers to about 10% pod stage. The disclosure provides methods that apply glyphosate at late stage *brassica* development.

13 Claims, 3 Drawing Sheets

GLYPHOSATE APPLICATION FOR WEED CONTROL IN *BRASSICA*

This application claims the benefit of U.S. Provisional Application No. 61/779,347, filed Mar. 13, 2013, the entire content which is herein incorporated by reference.

FIELD

The present disclosure relates to the field of agricultural biotechnology and more specifically, to the field of transgenic crop plants and timing of herbicide applications.

BACKGROUND

*Brassica* species are used world-wide as a source of vegetable oil, animal feeds, vegetables and condiments. The most economically important use of *Brassica* species is for the production of seed-derived, vegetable oils. *Brassica* species that are grown primarily for oil production are often called oilseed rape. In North America, canola, a type of oilseed rape that has been selected for low levels of erucic acid and glucosinolates in seeds, is the predominant *Brassica* plant grown for the production of vegetable oil for human consumption.

Biotechnology has been used in *Brassica* species for many reasons, including canola variety improvements, yield increase, stress tolerance, modified oil consumption, and other improved traits such as herbicide tolerance. Regarding herbicide tolerance in the commercial production of *brassica* crops, it is desirable to easily and quickly eliminate unwanted plants (i.e., "weeds") from the field of *Brassica* plants. An ideal treatment would be one which could be applied to an entire field but which would eliminate only the unwanted plants while leaving the crop plants unharmed. One such treatment system would involve the use of crop plants which are tolerant to one or more herbicide(s) so that when the herbicide was sprayed on a field of herbicide-tolerant crop plants, the crop plants would continue to thrive while non-herbicide-tolerant weeds were killed or severely damaged.

Because weed control is needed for profitable canola production in addition to other reasons, herbicide tolerant varieties of canola have been developed to be resistant/tolerant to certain herbicides. The ability of herbicide-resistant canola to control a broad spectrum of weeds has led to rapid adoption of the technology. Reduced tillage, increased yields, and improved weed control are several examples of the benefits of herbicide-resistant canola technology. However, it is known that the response of canola to herbicide applications is highly dependent on the herbicide resistant system that is being used in the particular field.

Three main groups of herbicide tolerant canola varieties exist and include, but are not limited to, glyphosate tolerant, glufosinate tolerant or imidazolinone tolerant varieties. The first two groups were developed using genetic modification while the third was developed using traditional plant breeding techniques. Triazine-tolerant canola has also been developed.

Strategic herbicide application timing in herbicide tolerant canola varieties results in economic impact for canola producers because weed density and weed biomass are major restraints in canola production. There is a possibility for several applications of herbicides in herbicide-resistant canola crops. For example, producers may apply an herbicide before planting as an alternative to tillage to manage weed emergence. Once the canola crop has emerged, herbicides may be applied to control post-emergent weeds. Crop staging is one of the major drivers for determining appropriate herbicide application timing in canola.

This disclosure relates to methods of applying glyphosate to improve weed control in a field containing herbicide tolerant *brassica* species, and more specifically, glyphosate tolerant *brassica* species.

SUMMARY

Methods for applying glyphosate to improve weed control in a field containing herbicide tolerant *brassica* species are provided herein.

A first aspect features a method of applying glyphosate to improve weed control in a field containing herbicide tolerant *brassica* species. The method comprises applying a glyphosate treatment comprising an effective amount of glyphosate over a population of glyphosate tolerant *brassica* plants, wherein a substantial portion of the *brassica* plants are at about the flowering stage exhibiting at least about 10% open flowers to about 10% pod stage or beyond the flowering stage and wherein a substantial portion of open flowers or pods do not show significant discoloration post-glyphosate treatment.

In an embodiment, the glyphosate tolerant *brassica* plants express a glyphosate acetyl transferase (GAT) enzyme.

In an embodiment, the glyphosate tolerant *brassica* plants express a glyphosate acetyl transferase (GAT) enzyme in combination with an enzyme that provides tolerance to glufosinate herbicide.

In an embodiment, the open flowers do not show significant discoloration within 5 days post-glyphosate treatment.

In an embodiment, the glyphosate treatment comprises in g acid equivalent/hectare of glyphosate as the active ingredient of about 675, 1350, 2025 or 2700 in a single application.

In an embodiment, the glyphosate treatment comprises up to about 5400 g acid equivalent/hectare of glyphosate as the active ingredient in one or more cumulative applications.

Another aspect features a method of applying glyphosate to improve weed control in a field containing glyphosate-tolerant *brassica* species. The method comprises applying one or more glyphosate treatments comprising an effective amount of glyphosate over a population of glyphosate tolerant *brassica* plants, wherein a substantial portion of the *brassica* plants are at a stage that is beyond the 6-leaf stage and wherein the glyphosate tolerance is due to the expression of a glyphosate metabolizing enzyme in the *brassica* plants; and obtaining *brassica* seeds from the *brassica* plants, wherein a substantial portion of pods are not aborted post-glyphosate treatment.

Another aspect features a method of preventing yield loss or yield penalty at harvest of *brassica* plants. The method comprises applying a first glyphosate treatment comprising an effective amount of glyphosate over a population of glyphosate tolerant *brassica* plants, wherein a substantial portion of the *brassica* plants are at the cotyledon stage and the *brassica* plants express a glyphosate metabolizing enzyme; applying one or more additional glyphosate treatments comprising an effective amount of glyphosate over a population of glyphosate tolerant *brassica* plants, wherein a substantial portion of the *brassica* plants are at a stage that is beyond the 6-leaf stage; and, obtaining *brassica* seeds from the *brassica* plants, wherein the yield loss is minimized due to a substantial reduction in discoloration or pod abortion after one or more late-stage applications of glyphosate.

In an embodiment, the *brassica* plants express glyphosate acetyl transferase (GAT).

In an embodiment, the average *brassica* yield is reduced by no more than 5% compared to a control treatment.

Another aspect of the disclosure features a method of weed control in a field. The method comprises planting a population of glyphosate tolerant *brassica* plants in the field, wherein the *brassica* plants express a glyphosate acetyl transferase enzyme; and, applying a glyphosate treatment to a *brassica* field containing one or more weeds, wherein a substantial portion of the *brassica* plants are at a late developmental stage selected from the group consisting of inflorescence emergence, flowering, seed development and ripening and thereby substantially reducing the growth of weeds in the *brassica* field.

Another aspect of the disclosure features a method of disease control of a glyphosate-tolerant *brassica* population in a field. The method comprises applying glyphosate treatment to the *brassica* population in the field, wherein the glyphosate treatment further comprises a disease control agent selected from the group consisting of insecticides, fungicides, and pesticides; and, wherein a substantial portion of the *brassica* population is beyond the 6-leaf stage and do not express an insensitive 5-enolpyruvylshikimate-3-phosphate synthase (EPSPS) and wherein the substantial portion of the *brassica* population does not show significant chlorosis.

In an embodiment, the glyphosate treatment is applied beyond the first flower stage.

In an embodiment, the glyphosate treatment is applied at about the 10% flower stage.

In another embodiment, the glyphosate treatment is applied from about Canola growth stage 60 to about 80 on the BBCH scale.

An aspect of the disclosure features a method of reducing weed matter during harvest of *brassica* seeds of a glyphosate-tolerant *brassica* population in a field. The method comprises applying a glyphosate treatment to the *brassica* population in the field, wherein the field has one or more weeds selected from the group consisting of thistle and pigweed, and wherein the *brassica* population is beyond the 6-leaf stage and the *brassica* population does not express an insensitive EPSPS; and controlling the growth of weed prior to harvest such that the weed mater is reduced at harvest.

An aspect of the disclosure features a method of late season weed control in a field having *brassica* crop without adversely affecting the yield. The method comprises planting a population of *brassica* plants that are tolerant to glyphosate wherein the plants express a glyphosate metabolizing enzyme such that the expression of the enzyme results in effective glyphosate tolerance; applying an effective amount of glyphosate to the *brassica* plants wherein a substantial portion of the *brassica* plants are beyond the 6-leaf stage and wherein the glyphosate application does not result in significant chlorosis; and controlling the growth of weeds in the field and wherein the *brassica* crop yield is not reduced by more than 5% compared to control *brassica* plants not expressing the glyphosate metabolizing enzyme.

In an embodiment, the glyphosate treatment comprises 1350-2700 g ae/hectare of glyphosate and a substantial portion of the *brassica* plants are at about 10% flower stage.

In another embodiment, the glyphosate application further comprises a disease control agent selected from the group consisting of insecticides, fungicides, and pesticides.

In another embodiment, the glyphosate application further comprises a late season nutrient application.

In another embodiment, the glyphosate is premixed with a disease control agent selected from the group consisting of insecticides, fungicides, and pesticides.

Another aspect of the disclosure features a method of increasing Canola seed purity. The method comprises planting a population of glyphosate tolerant Canola plants in a field; applying glyphosate to the field suspected of containing one or more non-Canola species, wherein the Canola plants metabolize glyphosate and do not express an insensitive EPSPS and wherein a substantial portion of the *brassica* plants are beyond the 6-leaf stage; and, improving the Canola seed purity by controlling the growth of non-Canola species by the late-season application of glyphosate.

Another aspect of the disclosure features a method of reducing harvest cost of *brassica*. The method comprises reducing the population of weeds in a *brassica* growing field by applying glyphosate to a population of glyphosate-tolerant *brassica* plants that exhibit at least 10% open flowers and harvesting the *brassica* crop, wherein the *brassica* plants express a glyphosate metabolizing enzyme.

In another embodiment, the glyphosate application does not result in a significant chlorosis or necrosis of the *brassica* plants.

In another embodiment, the glyphosate is inactivated within the *brassica* plants including the reproductive tissue.

Another aspect of the disclosure features a method of controlling weeds in a *brassica* field. The method comprises applying a second glyphosate treatment to a population of glyphosate-tolerant *brassica* plants, wherein a substantial portion of the *brassica* plants are at the reproductive growth stage and wherein the *brassica* plants express a glyphosate metabolizing enzyme.

In another embodiment, the glyphosate metabolizing enzyme is a GAT polypeptide.

In another embodiment, the glyphosate-tolerant *brassica* plants do not express an insensitive EPSPS.

In another embodiment, the second glyphosate treatment is at a lower dose than a first glyphosate treatment.

In another embodiment, the second glyphosate treatment is at a higher dose than a first glyphosate treatment.

BRIEF DESCRIPTION OF THE FIGURES

The disclosure can be more fully understood from the following detailed description and the accompanying drawings which form a part of this application.

DETAILED DESCRIPTION

Figure 1:
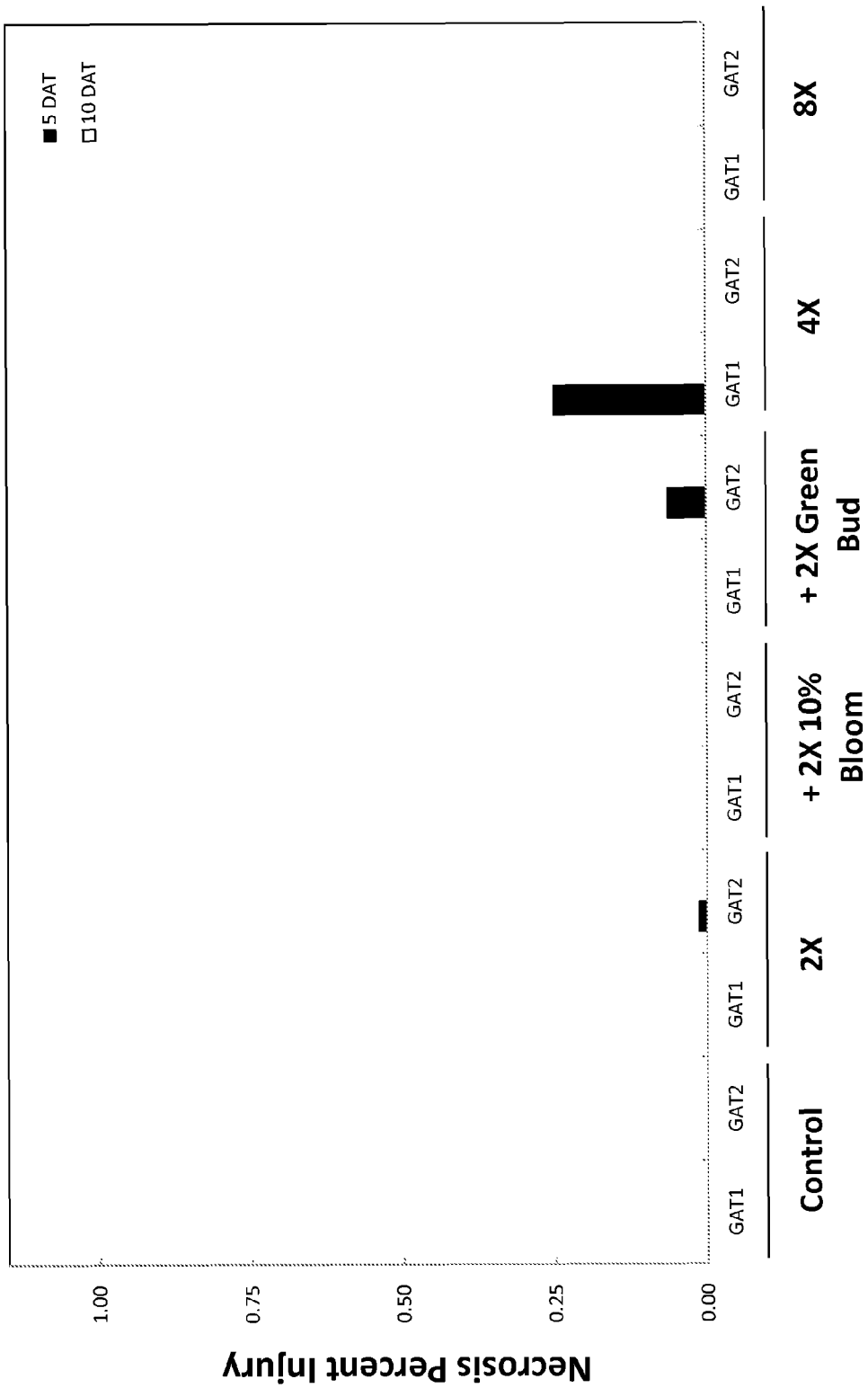
FIG. 1 shows herbicide efficacy data from glyphosate spray experiments. The figure represents eight transgenic lines. Necrosis percent crop response is indicated on the y axis and treatments are indicated on the x axis. Data is shown for 5 days after treatment and 10 days after treatment. "Control" represents treatment with conventional herbicides to reduce weeds in the control plots.

The present disclosure relates to methods of applying glyphosate to improve weed control in a field containing herbicide tolerant *brassica* species. In particular, glyphosate treatments are applied to a substantial portion of herbicide tolerant *brassica* plants which are beyond the 2-6 leaf stage such as for example to a substantial portion of herbicide tolerant *brassica* plants which are at the 10% open flowers to about 10% pod stage.

The present disclosures now will be described more fully hereinafter with reference to the accompanying drawings, in which some, but not all embodiments of the disclosures are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the disclosures set forth herein will come to mind to one skilled in the art to which these disclosures pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. Although specific terms are employed herein, they are used in a generic and descriptive sense only and not for purposes of limitation.

Units, prefixes, and symbols are denoted in their International System of Units (SI) accepted form. Unless otherwise indicated, nucleic acids are written left to right in 5' to 3' orientation; and amino acid sequences are written left to right in amino to carboxy orientation. Numeric ranges recited within the specification are inclusive of the numbers defining the range and include each integer within the defined range. Nucleotides may be referred to herein by their one-letter symbols recommended by the IUPAC-IUBMB Nomenclature Commission. The terms defined below are more fully defined by reference to the specification as a whole. Section headings provided throughout the specification are provided for convenience and are not limitations to the various objects and embodiments of the present disclosure.

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein, the term "comprising" means "including but not limited to."

As used herein, the term "*Brassica*" means any *Brassica* plant and includes all plant varieties that can be bred with *Brassica*.

As used herein, the term plant includes plant cells, plant organs, plant protoplasts, plant cell tissue cultures from which plants can be regenerated, plant calli, plant clumps and plant cells that are intact in plants or parts of plants such as embryos, pollen, ovules, seeds, leaves, flowers, branches, fruit, stalks, roots, root tips, anthers, and the like. Mature seed produced may be used for food, feed, fuel or other commercial or industrial purposes or for purposes of growing or reproducing the species. Progeny, variants and mutants of the regenerated plants are also included within the scope of the disclosure.

A transgenic "event" is produced by transformation of plant cells with a heterologous DNA construct(s) including a nucleic acid expression cassette that comprises a transgene of interest, the regeneration of a population of plants from cells which each comprise the inserted transgene and selection of a particular plant characterized by insertion into a particular genome location. An event is characterized phenotypically by the expression of the transgene(s). At the genetic level, an event is part of the genetic makeup of a plant. The term "event" also refers to progeny, produced by a sexual outcross between the transformant and another variety, that include the heterologous DNA. Even after repeated back-crossing to a recurrent parent, the inserted DNA and flanking DNA from the transformed parent are present in the progeny of the cross at the same chromosomal location. The term "event" also refers to DNA from the original transformant comprising the inserted DNA and flanking sequence immediately adjacent to the inserted DNA that would be expected to be transferred to a progeny as the result of a sexual cross of one parental line that includes the inserted DNA (e.g., the original transformant and progeny resulting from selfing) and a parental line that does not contain the inserted DNA.

Transgenic events expressing GAT1 and GAT2 genes were tested herein. GAT1, as mentioned herein is the *Brassica* GAT event DP-073496-4 (PCT International Patent Application No. PCT/US2010/058011, incorporated by reference). GAT2, as mentioned herein is another transgenic *Brassica* line expressing a GAT variant.

Unlike *brassica* plants expressing an insensitive EPSPS, GAT expressing *brassica* plants are rendered tolerant to glyphosate herbicide by the action of the glyphosate acetyl transferase enzyme that inactivates or detoxifies glyphosate in a single enzymatic step. Enzymatic N-acetylation of glyphosate results in the glyphosate tolerance of *brassica* plants disclosed herein.

Efficacy to glyphosate treatments with reduced/minimal discoloration (chlorosis) or necrosis at later reproductive stages (e.g., 10% open flowers) along with no significant reduction in seed yield of *brassica* is demonstrated herein.

The term "germplasm" refers to an individual, a group of individuals or a clone representing a genotype, variety, species or culture or the genetic material thereof.

The phrase "hybrid plants" refers to plants which result from a cross between genetically different individuals.

Plant injury may be measured using several parameters such as necrosis percent injury, and/or chlorosis percent injury.

Necrosis percent injury describes a visual rating based on the percentage of plants that have brown or yellowing spots as a result of herbicide treatment, where 100% represents a completely dead plant, and 0% indicates that brown or yellowing spots were absent in treated plants.

Chlorosis percent injury describes a visual rating of the percentage of the plant with a yellowing of the apical meristem, newest leaves or older leaves, where 100% denotes that all tissue is yellow, and 0% denotes the absence of yellowing tissue in plants treated with herbicide.

Percentage of yield relative to 2X describes the yield obtained for the GAT events treated with respective glyphosate herbicide treatments compared to the same GAT events subjected to a solution containing 2X glyphosate treatment at the 3 to 5 leaf stage, expressed as a percentage of the 2X treatment at the 3 to 5 leaf stage.

In an embodiment, glyphosate is inactivated by a glyphosate acetyl transferase enzyme within the *brassica* plants including the reproductive tissue such as open flowers and green buds.

Desiccation describes the process of chemically treating plants which an agent (Reglone®) that will accelerate seed drying and maturation.

As used herein, the term "stacked" includes having multiple traits present in the same plant (i.e., both traits are incorporated into the nuclear genome, one trait is incorporated into the nuclear genome and one trait is incorporated into the genome of a plastid, or both traits are incorporated into the genome of a plastid). In one non-limiting example, "stacked traits" comprise a molecular stack where the sequences are physically adjacent to each other. A trait, as used herein, refers to the phenotype derived from a particular sequence or groups of sequences. Co-transformation of genes can be carried out using single transformation vectors comprising multiple genes or genes carried separately on multiple vectors. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, International Publication Numbers WO 1999/25821, WO 1999/25854, WO 1999/25840, WO 1999/25855 and WO 1999/25853, the disclosures of each of which are herein incorporated by reference.

In one embodiment, the herbicide tolerant *brassica* species may comprise the *brassica* GAT1 event. The polynucleotides conferring the GAT1 event may be engineered into a molecular stack. The molecular stack may comprise at least one additional polynucleotide that confers tolerance to a second herbicide. The sequence may confer tolerance to glufosinate, and may comprise a pat gene. The additional polynucleotide may provide tolerance to ALS-inhibitor herbicides. The additional polynucleotide may provide tolerance to dicamba or auxin herbicides.

In other embodiments, the herbicide tolerant *brassica* species of the disclosure may comprise one or more traits of interest, and in more specific embodiments, the plant may be stacked with any combination of polynucleotide sequences of interest in order to create plants with a desired combination of traits.

A trait, as used herein, refers to the phenotype derived from a particular sequence or groups of sequences. For example, herbicide-tolerance polynucleotides may be stacked with any other polynucleotides encoding polypeptides having pesticidal and/or insecticidal activity, such as *Bacillus thuringiensis* toxic proteins (described in U.S. Pat. Nos. 5,366,892; 5,747,450; 5,737,514; 5,723,756; U.S. Pat. No. 5,593,881; Geiser, et al., (1986) *Gene* 48:109; Lee, et al., (2003) *Appl. Environ. Microbiol.* 69:4648-4657 (Vip3A); Galitzky, et al., (2001) *Acta Crystallogr. D. Biol. Crystallogr.* 57:1101-1109 (Cry3Bbl) and Herman, et al., (2004) *J. Agric. Food Chem.* 52:2726-2734 (CrylF)), lectins (Van Damme, et al., (1994) *Plant Mol. Biol.* 24:825, pentin (described in U.S. Pat. No. 5,981,722), and the like. The combinations generated can also include multiple copies of any one of the polynucleotides of interest.

The herbicide tolerant *brassica* species of the disclosure may contain stacks with other herbicide-tolerance traits to create a transgenic plant of the disclosure with further improved properties. Other herbicide-tolerance polynucleotides that could be used in such embodiments include those conferring tolerance to glyphosate by other modes of action, such as, for example, a gene that encodes a glyphosate oxido-reductase enzyme as described more fully in U.S. Pat. Nos. 5,776,760 and 5,463,175. Other traits that could be combined with an event of the disclosure include those derived from polynucleotides that confer on the plant the capacity to produce a higher level of 5-enolpyruvylshikimate-3-phosphate synthase (EPSPS), for example, as more fully described in U.S. Pat. Nos. 6,248,876 B1; 5,627,061; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E and 5,491,288 and International Publication Numbers WO 97/04103; WO 00/66746; WO 01/66704 and WO 00/66747. Other traits that could be combined with the event of the disclosure include those conferring tolerance to sulfonylurea and/or imidazolinone, for example, as described more fully in U.S. Pat. Nos. 5,605,011; 5,013,659; 5,141,870; 5,767,361; 5,731,180; 5,304,732; 4,761,373; 5,331,107; 5,928,937 and 5,378,824 and International Publication Number WO 96/33270.

The herbicide tolerant *brassica* species of the disclosure may contain stacks. Polynucleotides encoding polypeptides, alone or stacked with one or more additional insect resistance traits can be stacked with one or more additional input traits (e.g., herbicide resistance, fungal resistance, virus resistance, stress tolerance, disease resistance, male sterility, stalk strength, and the like) or output traits (e.g., increased yield, modified starches, improved oil profile, balanced amino acids, high lysine or methionine, increased digestibility, improved fiber quality, drought resistance, and the like). A complete agronomic package of improved crop quality with the ability to flexibly and cost effectively control any number of agronomic pests may be generated.

Transgenes useful for preparing transgenic plants include, but are not limited to, the following:

1. Transgenes Conferring Resistance to Insects or Disease:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example, Jones, et al., (1994) *Science* 266:789 (cloning of the tomato Cf-9 gene for resistance to *Cladosporium fulvum*); Martin, et al., (1993) *Science* 262: 1432 (tomato Pto gene for resistance to *Pseudomonas syringae* pv. tomato encodes a protein kinase); Mindrinos, et al., (1994) *Cell* 78:1089 (*Arabidopsis* RSP2 gene for resistance to *Pseudomonas syringae*), McDowell and Woffenden, (2003) *Trends Biotechnol.* 21(4):178-83 and Toyoda, et al., (2002) Transgenic Res. 11(6):567-82. A plant resistant to a disease is one that is more resistant to a pathogen as compared to the wild type plant.

(B) Genes encoding a *Bacillus thuringiensis* protein, a derivative thereof or a synthetic polypeptide modeled thereon. See, for example, Geiser, et al., (1986) *Gene* 48:109, who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC Accession Numbers 40098, 67136, 31995 and 31998. Other non-limiting examples of *Bacillus thuringiensis* transgenes being genetically engineered are given in the following patents and patent applications and hereby are incorporated by reference for this purpose: U.S. Pat. Nos. 5,188,960; 5,689,052; 5,880,275; 5,986,177; 6,023,013, 6,060,594, 6,063,597, 6,077,824, 6,620,988, 6,642,030, 6,713,259, 6,893,826, 7,105,332; 7,179,965, 7,208,474; 7,227,056, 7,288,643, 7,323,556, 7,329,736, 7,449,552, 7,468,278, 7,510,878, 7,521,235, 7,544,862, 7,605,304, 7,696,412, 7,629,504, 7,705,216, 7,772,465, 7,790,846, 7,858,849 and WO 1991/14778; WO 1999/31248; WO 2001/12731; WO 1999/24581 and WO 1997/40162, the disclosures of each of which are herein incorporated by reference.

(C) A polynucleotide encoding an insect-specific hormone or pheromone such as an ecdysteroid and juvenile hormone, a variant thereof, a mimetic based thereon or an antagonist or agonist thereof. See, for example, the disclosure by Hammock, et al., (1990) *Nature* 344:458, of baculovirus expression of cloned juvenile hormone esterase, an inactivator of juvenile hormone.

(D) A polynucleotide encoding an insect-specific peptide which, upon expression, disrupts the physiology of the affected pest. For example, see the disclosures of, Regan, (1994) *J. Biol. Chem.* 269:9 (expression cloning yields DNA coding for insect diuretic hormone receptor); Pratt, et al., (1989) *Biochem. Biophys. Res. Comm.* 163:1243 (an allostatin is identified in *Diploptera puntata*); Chattopadhyay, et al., (2004) *Critical Reviews in Microbiology* 30(1):33-54; Zjawiony, (2004) *J Nat Prod* 67(2):300-310; Carlini and Grossi-de-Sa, (2002) *Toxicon* 40(11):1515-1539; Ussuf, et al., (2001) *Curr Sci.* 80(7):847-853 and Vasconcelos and Oliveira, (2004) *Toxicon* 44(4):385-403. See also, U.S. Pat. No. 5,266,317 to Tomalski, et al., who disclose genes encoding insect-specific toxins.

(E) A polynucleotide encoding an enzyme responsible for a hyperaccumulation of a monoterpene, a sesquiterpene, a steroid, hydroxamic acid, a phenylpropanoid derivative or another non-protein molecule with insecticidal activity.

(F) A polynucleotide encoding an enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See, PCT Application WO 1993/02197 in the name of Scott, et al., which discloses the nucleotide sequence of a callase gene. DNA molecules which contain chitinase-encoding sequences can be obtained, for example, from the ATCC under Accession Numbers 39637 and 67152. See also, Kramer, et al., (1993) *Insect Biochem. Molec. Biol.* 23:691, who teach the nucleotide sequence of a cDNA encoding tobacco hookworm chitinase and Kawalleck et al., (1993) *Plant Molec. Biol.* 21:673, who provide the nucleotide sequence of the parsley ubi4-2 polyubiquitin gene, and U.S. Pat. Nos. 6,563,020; 7,145,060 and 7,087,810.

(G) A polynucleotide encoding a molecule that stimulates signal transduction. For example, see the disclosure by Botella, et al., (1994) *Plant Molec. Biol.* 24:757, of nucleotide sequences for mung bean calmodulin cDNA clones, and Griess, et al., (1994) *Plant Physiol.* 104:1467, who provide the nucleotide sequence of a maize calmodulin cDNA clone.

(H) A polynucleotide encoding a hydrophobic moment peptide. See, PCT Application WO 1995/16776 and U.S. Pat. No. 5,580,852 disclosure of peptide derivatives of Tachyplesin which inhibit fungal plant pathogens) and PCT Application WO 1995/18855 and U.S. Pat. No. 5,607,914 (teaches synthetic antimicrobial peptides that confer disease resistance).

(I) A polynucleotide encoding a membrane permease, a channel former or a channel blocker. For example, see the disclosure by Jaynes, et al., (1993) *Plant Sci.* 89:43, of heterologous expression of a cecropin-beta lytic peptide analog to render transgenic tobacco plants resistant to *Pseudomonas solanacearum*.

(J) A gene encoding a viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., (1990) *Ann. Rev. Phytopathol.* 28:451. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) A polynucleotide encoding a developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See, Lamb, et al., (1992) *Bio/Technology* 10:1436. The cloning and characterization of a gene which encodes a bean endopolygalacturonase-inhibiting protein is described by Toubart, et al., (1992) *Plant J.* 2:367.

(L) A polynucleotide encoding a developmental-arrestive protein produced in nature by a plant. For example, Logemann, et al., (1992) *Bio/Technology* 10:305, have shown that transgenic plants expressing the barley ribosome-inactivating gene have an increased resistance to fungal disease.

(M) Genes involved in the Systemic Acquired Resistance (SAR) Response and/or the pathogenesis related genes. Briggs, (1995) *Current Biology* 5(2), Pieterse and Van Loon, (2004) *Curr. Opin. Plant Bio.* 7(4):456-64 and Somssich, (2003) *Cell* 113(7):815-6.

(N) Antifungal genes (Cornelissen and Melchers, (1993) *Pl. Physiol.* 101:709-712 and Parijs, et al., (1991) *Planta* 183:258-264 and Bushnell, et al., (1998) *Can. J. of Plant Path.* 20(2):137-149. Also see, U.S. patent application Ser. Nos. 09/950,933; 11/619,645; 11/657,710; 11/748,994; 11/774,121 and U.S. Pat. Nos. 6,891,085 and 7,306,946. LysM Receptor-like kinases for the perception of chitin fragments as a first step in plant defense response against fungal pathogens (US 2012/0110696).

(O) Detoxification genes, such as for fumonisin, beauvericin, moniliformin and zearalenone and their structurally related derivatives. For example, see, U.S. Pat. Nos. 5,716,820; 5,792,931; 5,798,255; 5,846,812; 6,083,736; 6,538,177; 6,388,171 and 6,812,380.

(P) A polynucleotide encoding a Cystatin and cysteine proteinase inhibitors. See, U.S. Pat. No. 7,205,453.

(Q) Defensin genes. See, WO 2003/000863 and U.S. Pat. Nos. 6,911,577; 6,855,865; 6,777,592 and 7,238,781.

(R) Genes conferring resistance to nematodes. See, e.g., PCT Application WO 1996/30517; PCT Application WO 1993/19181, WO 2003/033651 and Urwin, et al., (1998) *Planta* 204:472-479, Williamson, (1999) *Curr Opin Plant Bio.* 2(4):327-31; U.S. Pat. Nos. 6,284,948 and 7,301,069 and miR164 genes (WO 2012/058266).

(S) Genes that confer resistance to *Phytophthora* Root Rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker, et al., *Phytophthora* Root Rot Resistance Gene Mapping in Soybean, Plant Genome IV Conference, San Diego, Calif. (1995).

(T) Genes that confer resistance to Brown Stem Rot, such as described in U.S. Pat. No. 5,689,035 and incorporated by reference for this purpose.

(U) Genes that confer resistance to *Colletotrichum*, such as described in US Patent Application Publication US 2009/0035765 and incorporated by reference for this purpose. This includes the Rcg locus that may be utilized as a single locus conversion.

2. Transgenes that Confer Resistance to an Herbicide:

(A) A polynucleotide encoding resistance to an herbicide that inhibits the growing point or meristem, such as an imidazolinone or a sulfonylurea. Exemplary genes in this category code for mutant ALS and AHAS enzyme as described, for example, by Lee, et al., (1988) *EMBO J.* 7:1241 and Miki, et al., (1990) *Theor. Appl. Genet.* 80:449, respectively. See also, U.S. Pat. Nos. 5,605,011; 5,013,659; 5,141,870; 5,767,361; 5,731,180; 5,304,732; 4,761,373; 5,331,107; 5,928,937 and 5,378,824; U.S. patent application Ser. No. 11/683,737 and International Publication WO 1996/33270.

(B) A polynucleotide encoding a protein for resistance to Glyphosate (resistance imparted by mutant 5-enolpyruvyl-shikimate-3-phosphate synthase (EPSPS) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627,061 to Barry, et al., also describes genes encoding EPSPS enzymes. See also, U.S. Pat. Nos. 6,566,587; 6,338,961; 6,248,876 B1; 6,040,497; 5,804,425; 5,633,435; 5,145,783; 4,971,908; 5,312,910; 5,188,642; 5,094,945, 4,940,835; 5,866,775; 6,225,114 B1; 6,130,366; 5,310,667; 4,535,060; 4,769,061; 5,633,448; 5,510,471; Re. 36,449; RE 37,287 E and 5,491,288 and International Publications EP 1173580; WO 2001/66704; EP 1173581 and EP 1173582, which are incorporated herein by reference for this purpose. Glyphosate resistance is also imparted to plants that express a gene encoding a glyphosate oxido-reductase enzyme as described more fully in U.S. Pat. Nos. 5,776,760 and 5,463,175, which are incorporated herein by reference for this purpose. In addition glyphosate resistance can be imparted to plants by the over expression of genes encoding glyphosate N-acetyl-transferase. See, for example, U.S. Pat. Nos. 7,462,481; 7,405,074 and US Patent Application Publication Number US 2008/0234130. A DNA molecule encoding a mutant aroA gene can be obtained under ATCC Accession Number 39256, and the nucleotide sequence of the mutant gene is disclosed in U.S. Pat. No. 4,769,061 to Comai. EP Application Number 0 333 033 to Kumada, et al., and U.S. Pat. No. 4,975,374 to Goodman, et al., disclose nucleotide sequences of glutamine synthetase genes which confer resistance to herbicides such as L-phosphinothricin. The nucleotide sequence of a phosphinothricin-acetyl-transferase gene is provided in EP Application Numbers 0 242 246 and 0 242 236 to Leemans, et al.; De Greef, et al., (1989) *Bio/Technology* 7:61, describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 B1 and 5,879,903, which are incorporated herein by reference for this purpose. Exemplary genes conferring resistance to phenoxy proprionic acids and cyclohexones, such as sethoxydim and haloxyfop, are the Accl-S1, Accl-S2 and Accl-S3 genes described by Marshall, et al., (1992) *Theor. Appl. Genet.* 83:435.

(C) A polynucleotide encoding a protein for resistance to herbicide that inhibits photosynthesis, such as a triazine (psbA and gs+ genes) and a benzonitrile (nitrilase gene). Przibilla, et al., (1991) Plant Cell 3:169, describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC Accession Numbers 53435, 67441 and 67442. Cloning and expression of DNA coding for a glutathione S-transferase is described by Hayes, et al., (1992) *Biochem. J.* 285:173.

(D) A polynucleotide encoding a protein for resistance to Acetohydroxy acid synthase, which has been found to make plants that express this enzyme resistant to multiple types of herbicides, has been introduced into a variety of plants (see, e.g., Hattori, et al., (1995) Mol Gen Genet. 246:419). Other genes that confer resistance to herbicides include: a gene encoding a chimeric protein of rat cytochrome P4507A1 and yeast NADPH-cytochrome P450 oxidoreductase (Shiota, et al., (1994) *Plant Physiol* 106:17), genes for glutathione reductase and superoxide dismutase (Aono, et al., (1995) *Plant Cell Physiol* 36:1687) and genes for various phosphotransferases (Datta, et al., (1992) *Plant Mol Biol* 20:619).

(E) A polynucleotide encoding resistance to an herbicide targeting Protoporphyrinogen oxidase (protox) which is necessary for the production of chlorophyll. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306 B1; 6,282,837 B1 and 5,767,373 and International Publication WO 2001/12825.

(F) The aad-1 gene (originally from *Sphingobium herbicidovorans*) encodes the aryloxyalkanoate dioxygenase (AAD-1) protein. The trait confers tolerance to 2,4-dichlorophenoxyacetic acid and aryloxyphenoxypropionate (commonly referred to as "fop" herbicides such as quizalofop) herbicides. The aad-1 gene, itself, for herbicide tolerance in plants was first disclosed in WO 2005/107437 (see also, US 2009/0093366). The aad-12 gene, derived from *Delftia acidovorans*, which encodes the aryloxyalkanoate dioxygenase (AAD-12) protein that confers tolerance to 2,4-dichlorophenoxyacetic acid and pyridyloxyacetate herbicides by deactivating several herbicides with an aryloxyalkanoate moiety, including phenoxy auxin (e.g., 2,4-D, MCPA), as well as pyridyloxy auxins (e.g., fluroxypyr, triclopyr).

(G) A polynucleotide encoding an herbicide resistant dicamba monooxygenase disclosed in US Patent Application Publication 2003/0135879 for imparting dicamba tolerance;

(H) A polynucleotide molecule encoding bromoxynil nitrilase (Bxn) disclosed in U.S. Pat. No. 4,810,648 for imparting bromoxynil tolerance;

(I) A polynucleotide molecule encoding phytoene (crtI) described in Misawa, et al., (1993) *Plant J.* 4:833-840 and in Misawa, et al., (1994) *Plant J.* 6:481-489 for norflurazon tolerance.

3. Transgenes Conferring or Contributing to an Altered Grain Characteristic (A) Altered fatty acids, for example, by (1) Down-regulation of stearoyl-ACP to increase stearic acid content of the plant. See, Knultzon, et al., (1992) *Proc. Natl. Acad. Sci. USA* 89:2624 and WO 1999/64579 (Genes to Alter Lipid Profiles in Corn).

(2) Elevating oleic acid via FAD-2 gene modification and/or decreasing linolenic acid via FAD-3 gene modification (see, U.S. Pat. Nos. 6,063,947; 6,323,392; 6,372,965 and WO 1993/11245).

(3) Altering conjugated linolenic or linoleic acid content, such as in WO 2001/12800.

(4) Altering LEC1, AGP, Dek1, Superal1, mil ps, various Ipa genes such as Ipa1, Ipa3, hpt or hggt. For example, see, WO 2002/42424, WO 1998/22604, WO 2003/011015, WO 2002/057439, WO 2003/011015, U.S. Pat. Nos. 6,423,886, 6,197,561, 6,825,397 and US Patent Application Publication Numbers US 2003/0079247, US 2003/0204870 and Rivera-Madrid, et al., (1995) *Proc. Natl. Acad. Sci.* 92:5620-5624.

(5) Genes encoding delta-8 desaturase for making long-chain polyunsaturated fatty acids (U.S. Pat. No. 8,058,571), delta-9 desaturase for lowering saturated fats (U.S. Pat. No. 8,063,269), Primula Δ6-desaturase for improving omega-3 fatty acid profiles.

(6) Isolated nucleic acids and proteins associated with lipid and sugar metabolism regulation, in particular, lipid metabolism protein (LMP) used in methods of producing transgenic plants and modulating levels of seed storage compounds including lipids, fatty acids, starches or seed storage proteins and use in methods of modulating the seed size, seed number, seed weights, root length and leaf size of plants (EP 2404499).

(7) Altering expression of a High-Level Expression of Sugar-Inducible 2 (HSI2) protein in the plant to increase or decrease expression of HSI2 in the plant. Increasing expression of HSI2 increases oil content while decreasing expression of HSI2 decreases abscisic acid sensitivity and/or increases drought resistance (US Patent Application Publication Number 2012/0066794).

(B) Altered phosphorus content, for example, by the (1) Introduction of a phytase-encoding gene would enhance breakdown of phytate, adding more free phosphate to the transformed plant. For example, see, Van Hartingsveldt, et al., (1993) *Gene* 127:87, for a disclosure of the nucleotide sequence of an *Aspergillus niger* phytase gene.

(2) Modulating a gene that reduces phytate content. In maize, this, for example, could be accomplished, by cloning and then re-introducing DNA associated with one or more of the alleles, such as the LPA alleles, identified in maize mutants characterized by low levels of phytic acid, such as in WO 2005/113778 and/or by altering inositol kinase activity as in WO 2002/059324, US Patent Application Publication Number 2003/0009011, WO 2003/027243, US Patent Application Publication Number 2003/0079247, WO 1999/05298, U.S. Pat. No. 6,197,561, U.S. Pat. No. 6,291,224, U.S. Pat. No. 6,391,348, WO 2002/059324, US Patent Application Publication Number 2003/0079247, WO 1998/45448, WO 1999/55882, WO 2001/04147.

(C) Altered carbohydrates affected, for example, by altering a gene for an enzyme that affects the branching pattern of starch or, a gene altering thioredoxin such as NTR and/or TRX (see, U.S. Pat. No. 6,531,648, which is incorporated by reference for this purpose) and/or a gamma zein knock out or mutant such as cs27 or TUSC27 or en27 (see, U.S. Pat. No. 6,858,778 and US Patent Application Publication Number 2005/0160488, US Patent Application Publication Number 2005/0204418, which are incorporated by reference for this purpose). See, Shiroza, et al., (1988) *J. Bacteriol.* 170:810 (nucleotide sequence of *Streptococcus* mutant fructosyltransferase gene), Steinmetz, et al., (1985) *Mol. Gen. Genet.* 200:220 (nucleotide sequence of *Bacillus subtilis* levansucrase gene), Pen, et al., (1992) *Bio/Technology* 10:292 (production of transgenic plants that express *Bacillus licheniformis* alpha-amylase), Elliot, et al., (1993) *Plant Molec. Biol.* 21:515 (nucleotide sequences of tomato invertase genes), Søgaard, et al., (1993) *J. Biol. Chem.* 268:22480 (site-directed mutagenesis of barley alpha-amylase gene) and Fisher, et al., (1993) *Plant Physiol.* 102:1045 (maize endosperm starch branching enzyme II), WO 1999/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)). The fatty acid modification genes mentioned herein may also be used to affect starch content and/or composition through the interrelationship of the starch and oil pathways.

(D) Altered antioxidant content or composition, such as alteration of tocopherol or tocotrienols. For example, see, U.S. Pat. No. 6,787,683, US Patent Application Publication Number 2004/0034886 and WO 2000/68393 involving the manipulation of antioxidant levels and WO 2003/082899 through alteration of a homogentisate geranyl geranyl transferase (hggt).

(E) Altered essential seed amino acids. For example, see, U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO 1999/40209 (alteration of amino acid compositions in seeds), WO 1999/29882 (methods for altering amino acid content of proteins), U.S. Pat. No. 5,850,016 (alteration of amino acid compositions in seeds), WO 1998/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO 1998/56935 (plant amino acid biosynthetic enzymes), WO 1998/45458 (engineered seed protein having higher percentage of essential amino acids), WO 1998/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO 1996/01905 (increased threonine), WO 1995/15392 (increased lysine), US Patent Application Publication Number 2003/0163838, US Patent Application Publication Number 2003/0150014, US Patent Application Publication Number 2004/0068767, U.S. Pat. No. 6,803,498, WO 2001/79516.

4. Genes Creating a Site for Site-Specific DNA Integration.

This includes the introduction of FRT sites that may be used in the FLP/FRT system and/or Lox sites that may be used in the Cre/Loxp system. For example, see, Lyznik, et al., (2003) *Plant Cell Rep* 21:925-932 and WO 1999/25821, which are hereby incorporated by reference. Other systems that may be used include the Gin recombinase of phage Mu (Maeser, et al., (1991) Vicki Chandler, The Maize Handbook ch. 118 (Springer-Verlag 1994), the Pin recombinase of *E. coli* (Enomoto, et al., 1983) and the R/RS system of the pSRi plasmid (Araki, et al., 1992).

5. Genes Affecting Abiotic Stress Resistance

Including but not limited to flowering, ear and seed development, enhancement of nitrogen utilization efficiency, altered nitrogen responsiveness, drought resistance or tolerance, heat resistance or tolerance, cold resistance or tolerance and salt resistance or tolerance and increased yield under stress.

(A) For example, see: WO 2000/73475 where water use efficiency is altered through alteration of malate; U.S. Pat. Nos. 5,892,009, 5,965,705, 5,929,305, 5,891,859, 6,417, 428, 6,664,446, 6,706,866, 6,717,034, 6,801,104, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 199809521.

(B) WO 199938977 describing genes, including CBF genes and transcription factors effective in mitigating the negative effects of freezing, high salinity and drought on plants, as well as conferring other positive effects on plant phenotype.

(C) US Patent Application Publication Number 2004/0148654 and WO 2001/36596 where abscisic acid is altered in plants resulting in improved plant phenotype such as increased yield and/or increased tolerance to abiotic stress.

(D) WO 2000/006341, WO 2004/090143, U.S. Pat. Nos. 7,531,723 and 6,992,237 where cytokinin expression is modified resulting in plants with increased stress tolerance, such as drought tolerance, and/or increased yield. Also see, WO 2002/02776, WO 2003/052063, JP 2002/281975, U.S. Pat. No. 6,084,153, WO 2001/64898, U.S. Pat. No. 6,177,275 and U.S. Pat. No. 6,107,547 (enhancement of nitrogen utilization and altered nitrogen responsiveness).

(E) For ethylene alteration, see, US Patent Application Publication Number 2004/0128719, US Patent Application Publication Number 2003/0166197 and WO 2000/32761.

(F) For plant transcription factors or transcriptional regulators of abiotic stress, see, e.g., US Patent Application Publication Number 2004/0098764 or US Patent Application Publication Number 2004/0078852.

(G) Genes that increase expression of vacuolar pyrophosphatase such as AVP1 (U.S. Pat. No. 8,058,515) for increased yield; nucleic acid encoding a HSFA4 or a HSFA5 (Heat Shock Factor of the class A4 or A5) polypeptides, an oligopeptide transporter protein (OPT4-like) polypeptide; a plastochron2-like (PLA2-like) polypeptide or a Wuschel related homeobox 1-like (WOX1-like) polypeptide (U. Patent Application Publication Number US 2011/0283420).

(H) Down regulation of polynucleotides encoding poly (ADP-ribose) polymerase (PARP) proteins to modulate programmed cell death (U.S. Pat. No. 8,058,510) for increased vigor.

(I) Polynucleotide encoding DTP21 polypeptides for conferring drought resistance (US Patent Application Publication Number US 2011/0277181).

(J) Nucleotide sequences encoding ACC Synthase 3 (ACS3) proteins for modulating development, modulating response to stress, and modulating stress tolerance (US Patent Application Publication Number US 2010/0287669).

(K) Polynucleotides that encode proteins that confer a drought tolerance phenotype (DTP) for conferring drought resistance (WO 2012/058528).

Other genes and transcription factors that affect plant growth and agronomic traits such as yield, flowering, plant growth and/or plant structure, can be introduced or introgressed into plants, see e.g., WO 1997/49811 (LHY), WO 1998/56918 (ESD4), WO 1997/10339 and U.S. Pat. No. 6,573,430 (TFL), U.S. Pat. No. 6,713,663 (FT), WO 1996/14414 (CON), WO 1996/38560, WO 2001/21822 (VRN1), WO 2000/44918 (VRN2), WO 1999/49064 (GI), WO 2000/46358 (FR1), WO 1997/29123, U.S. Pat. No. 6,794,560, U.S. Pat. No. 6,307,126 (GAI), WO 1999/09174 (D8 and Rht) and WO 2004/076638 and WO 2004/031349 (transcription factors).

6. Genes Conferring Increased Yield (A) A transgenic crop plant transformed by a 1-Amino-Cyclopropane-1-Carboxylate Deaminase-like Polypeptide (ACCDP) coding nucleic acid, wherein expression of the nucleic acid sequence in the crop plant results in the plant's increased root growth, and/or increased yield, and/or increased tolerance to environmental stress as compared to a wild type variety of the plant (U.S. Pat. No. 8,097,769).

(B) Over-expression of maize zinc finger protein gene (Zm-ZFP1) using a seed preferred promoter has been shown to enhance plant growth, increase kernel number and total kernel weight per plant (US Patent Application Publication Number 2012/0079623).

(C) Constitutive over-expression of maize lateral organ boundaries (LOB) domain protein (Zm-LOBDP1) has been shown to increase kernel number and total kernel weight per plant (US Patent Application Publication Number 2012/0079622).

(D) Enhancing yield-related traits in plants by modulating expression in a plant of a nucleic acid encoding a VIM1 (Variant in Methylation 1)-like polypeptide or a VTC2-like (GDP-L-galactose phosphorylase) polypeptide or a DUF1685 polypeptide or an ARF6-like (Auxin Responsive Factor) polypeptide (WO 2012/038893).

(E) Modulating expression in a plant of a nucleic acid encoding a Ste20-like polypeptide or a homologue thereof gives plants having increased yield relative to control plants (EP 2431472).

One of ordinary skill in the art is familiar with protocols for simulating drought conditions and for evaluating drought tolerance of plants that have been subjected to simulated or naturally-occurring drought conditions. For example, one can simulate drought conditions by giving plants less water than normally required or no water over a period of time, and one can evaluate drought tolerance by looking for differences in physiological and/or physical condition, including (but not limited to) vigor, growth, size, or root length, or in particular, leaf color or leaf area size. Other techniques for evaluating drought tolerance include measuring chlorophyll fluorescence, photosynthetic rates and gas exchange rates.

A drought stress experiment may involve a chronic stress (i.e., slow dry down) and/or may involve two acute stresses (i.e., abrupt removal of water) separated by a day or two of recovery.

Herbicide Tolerance Traits

The *brassica* species of the disclosure may be stacked with, for example, hydroxyphenylpyruvatedioxygenases which are enzymes that catalyze the reaction in which para-hydroxyphenylpyruvate (HPP) is transformed into homogentisate. Molecules which inhibit this enzyme and which bind to the enzyme in order to inhibit transformation of the HPP into homogentisate are useful as herbicides.

Traits conferring tolerance to such herbicides in plants are described in U.S. Pat. Nos. 6,245,968 B1; 6,268,549 and 6,069,115 and International Publication Number WO 99/23886. Other examples of suitable herbicide-tolerance traits that could be stacked with an event of the disclosure include aryloxyalkanoate dioxygenase polynucleotides (which reportedly confer tolerance to 2,4-D and other phenoxy auxin herbicides as well as to aryloxyphenoxypropionate herbicides as described, for example, in International Publication WO 05/107437) and dicamba-tolerance polynucleotides as described, for example, in Herman, et al., (2005) *J. Biol. Chem.* 280:24759-24767.

Other examples of herbicide-tolerance traits that could be stacked include those conferred by polynucleotides encoding an exogenous phosphinothricin acetyltransferase, as described in U.S. Pat. Nos. 5,969,213; 5,489,520; 5,550, 318; 5,874,265; 5,919,675; 5,561,236; 5,648,477; 5,646, 024; 6,177,616 and 5,879,903. Plants containing an exogenous phosphinothricin acetyltransferase can exhibit improved tolerance to glufosinate herbicides, which inhibit the enzyme glutamine synthase. Other examples of herbicide-tolerance traits that could be combined with an event disclosed herein include those conferred by polynucleotides conferring altered protoporphyrinogen oxidase (protox) activity, as described in U.S. Pat. Nos. 6,288,306 B1; 6,282,837 B1 and 5,767,373 and International Publication Number WO 01/12825. Plants containing such polynucleotides can exhibit improved tolerance to any of a variety of herbicides which target the protox enzyme (also referred to as "protox inhibitors").

ALS inhibitor-tolerant traits may be stacked with the plants disclosed herein. As used herein, an "ALS inhibitor-tolerant polypeptide" comprises any polypeptide which when expressed in a plant confers tolerance to at least one ALS inhibitor. A variety of ALS inhibitors are known and include, for example, sulfonylurea, imidazolinone, triazolopyrimidines, pryimidinyloxy(thio)benzoates, and/or sulfonylaminocarbonyltriazolinone herbicide. Additional ALS inhibitors are known and are disclosed elsewhere herein. It is known in the art that ALS mutations fall into different classes with regard to tolerance to sulfonylureas, imidazolinones, triazolopyrimidines, and pyrimidinyl(thio)benzoates, including mutations having the following characteristics: (1) broad tolerance to all four of these groups; (2) tolerance to imidazolinones and pyrimidinyl(thio)benzoates; (3) tolerance to sulfonylureas and triazolopyrimidines; and (4) tolerance to sulfonylureas and imidazolinones.

Various ALS inhibitor-tolerant polypeptides can be employed. The ALS inhibitor-tolerant polynucleotides contain at least one nucleotide mutation resulting in one amino acid change in the ALS polypeptide. The change occurs in one of seven substantially conserved regions of acetolactate synthase. See, for example, Hattori et al. (1995) *Molecular Genetics and Genomes* 246:419-425; Lee et al. (1998) *EMBO Journal* 7:1241-1248; Mazur et al. (1989) *Ann. Rev. Plant Phys.* 40:441-470; and U.S. Pat. No. 5,605,011, each of which is incorporated by reference in their entirety. The ALS inhibitor-tolerant polypeptide can be encoded by, for example, the SuRA or SuRB locus of ALS. In specific embodiments, the ALS inhibitor-tolerant polypeptide comprises the C3 ALS mutant, the HRA ALS mutant, the S4 mutant or the S4/HRA mutant or any combination thereof. Different mutations in ALS are known to confer tolerance to different herbicides and groups (and/or subgroups) of herbicides; see, e.g., Tranel and Wright (2002) *Weed Science* 50:700-712. See also, U.S. Pat. Nos. 5,605,011, 5,378,824, 5,141,870, and 5,013,659, each of which is herein incorporated by reference in their entirety. See also, SEQ ID NO:65 comprising a soybean HRA sequence; SEQ ID NO:66 comprising a maize HRA sequence; SEQ ID NO:67 comprising an *Arabidopsis* HRA sequence; and SEQ ID NO:86 comprising an HRA sequence used in cotton. The HRA mutation in ALS finds particular use. The mutation results in the production of an acetolactate synthase polypeptide which is resistant to at least one ALS inhibitor chemistry in comparison to the wild-type protein. For example, a plant expressing an ALS inhibitor-tolerant polypeptide may be tolerant of a dose of sulfonylurea, imidazolinone, triazolopyrimidines, pryimidinyloxy(thio)benzoates, and/or sulfonylaminocarbonyltriazolinone herbicide that is at least 2, 3, 4, 5, 6, 7, 8, 9, 10, 15, 20, 25, 30, 35, 40, 50, 70, 80, 100, 125, 150, 200, 500, or 1000 times higher than a dose of the herbicide that would cause damage to an appropriate control plant. The ALS inhibitor-tolerant polypeptide comprises a number of mutations. Additionally, plants having an ALS inhibitor polypeptide can be generated through the selection of naturally occurring mutations that impart tolerance to glyphosate.

The ALS inhibitor-tolerant polypeptide may confer tolerance to sulfonylurea and imidazolinone herbicides. Sulfonylurea and imidazolinone herbicides inhibit growth of higher plants by blocking acetolactate synthase (ALS), also known as, acetohydroxy acid synthase (AHAS). For example, plants containing particular mutations in ALS (e.g., the S4 and/or HRA mutations) are tolerant to sulfonylurea herbicides. The production of sulfonylurea-tolerant plants and imidazolinone-tolerant plants is described more fully in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270, which are incorporated herein by reference in their entireties for all purposes. The ALS inhibitor-tolerant polypeptide may comprise a sulfonamide-tolerant acetolactate synthase (otherwise known as a sulfonamide-tolerant acetohydroxy acid synthase) or an imidazolinone-tolerant acetolactate synthase (otherwise known as an imidazolinone-tolerant acetohydroxy acid synthase).

The glyphosate tolerant *brassica* plants express a glyphosate acetyl transferase (GAT) enzyme that may be combined, or stacked, with an EPSPS enzyme.

Other examples of herbicide-tolerance traits that could be combined in the *brassica* tolerant species disclosed herein include those conferring tolerance to at least one herbicide in a plant such as, for example, a *brassica* plant or horseweed. Herbicide-tolerant weeds are known in the art, as are plants that vary in their tolerance to particular herbicides. See, e.g., Green and Williams, (2004) "Correlation of Corn (*Zea mays*) Inbred Response to Nicosulfuron and Mesotrione," poster presented at the WSSA Annual Meeting in Kansas City, Mo., Feb. 9-12, 2004; Green, (1998) *Weed Technology* 12:474-477; Green and Ulrich, (1993) *Weed Science* 41:508-516. The trait(s) responsible for these tolerances can be combined by breeding or via other methods with an event disclosed herein to provide a plant of the disclosure as well as methods of use thereof.

A *brassica* tolerant species disclosed herein can contain at least one other trait to which results in a variety of desired trait combinations including, but not limited to, traits desirable for animal feed such as high oil content (e.g., U.S. Pat. No. 6,232,529); balanced amino acid content (e.g., hordothionins (U.S. Pat. Nos. 5,990,389; 5,885,801; 5,885,802 and 5,703,409; U.S. Pat. No. 5,850,016); barley high lysine (Williamson, et al., (1987) *Eur. J. Biochem.* 165:99-106 and WO 98/20122) and high methionine proteins (Pedersen, et al., (1986) *J. Biol. Chem.* 261:6279; Kirihara, et al., (1988) *Gene* 71:359 and Musumura, et al., (1989) *Plant Mol. Biol.* 12:123)); increased digestibility (e.g., modified storage proteins (U.S. patent application Ser. No. 10/053,410, filed Nov. 7, 2001) and thioredoxins (U.S. application Ser. No. 10/005, 429, filed Dec. 3, 2001)); the disclosures of which are herein incorporated by reference. Desired trait combinations also include LLNC (low linolenic acid content; see, e.g., Dyer, et al., (2002) *Appl. Microbiol. Biotechnol.* 59:224-230) and OLCH (high oleic acid content; see, e.g., Fernandez-Moya, et al., (2005) *J. Agric. Food Chem.* 53:5326-5330).

A *brassica* tolerant species disclosed herein can additionally contain other desirable traits such as, for example, fumonisin detoxification genes (U.S. Pat. No. 5,792,931), avirulence and disease resistance genes (Jones, et al., (1994) *Science* 266:789; Martin, et al., (1993) *Science* 262:1432; Mindrinos, et al., (1994) *Cell* 78:1089) and traits desirable for processing or process products such as modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)) and polymers or bioplastics (e.g., U.S. Pat. No. 5,602,321; beta-ketothiolase, polyhydroxybutyrate synthase, and acetoacetyl-CoA reductase (Schubert, et al., (1988) *J. Bacteriol.* 170:5837-5847) facilitate expression of polyhydroxyalkanoates (PHAs)); the disclosures of which are herein incorporated by reference. One could also combine herbicide-tolerant polynucleotides with polynucleotides providing agronomic traits such as male sterility (e.g., see, U.S. Pat. No. 5,583,210), stalk strength, flowering time or transformation technology traits such as cell cycle regulation or gene targeting (e.g., WO 99/61619, WO 00/17364 and WO 99/25821), the disclosures of which are herein incorporated by reference.

These stacked combinations can be created by any method including, but not limited to, breeding plants by any conventional methodology or genetic transformation. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855 and WO99/25853, all of which are herein incorporated by reference.

It is to be understood that as used herein the term "transgenic" includes any cell, cell line, callus, tissue, plant part or plant, the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition or spontaneous mutation.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere, et al., (1987) *Meth. Enzymol.* 143:277) and particle-accelerated or "gene gun" transformation technology (Klein, et al., (1987) *Nature* (London) 327:70-73; U.S. Pat. No. 4,945,050, incorporated herein by reference). Additional transformation methods are disclosed below.

The present disclosure provides methods for controlling weeds in an area of cultivation, preventing the development or the appearance of herbicide resistant weeds in an area of cultivation, producing a crop and increasing crop safety. The term "controlling," and derivations thereof, for example, as in "controlling weeds" refers to one or more of inhibiting the growth, germination, reproduction and/or proliferation of and/or killing, removing, destroying or otherwise diminishing the occurrence and/or activity of a weed.

As used herein, an "area of cultivation" comprises any region in which one desires to grow a plant. Such areas of cultivations include, but are not limited to, a field in which a plant is cultivated (such as a crop field, a sod field, a tree field, a managed forest, a field for culturing fruits and vegetables, etc), a greenhouse, a growth chamber, etc. Unless specified otherwise, for example in a particular experiment, a "control" or "control plant" or "control plant cell" provides a reference point for measuring changes in phenotype of the subject plant or plant cell, and may be any suitable plant or plant cell. A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell which is genetically identical to the subject plant or plant cell but which is not exposed to the same treatment (e.g., herbicide treatment) as the subject plant or plant cell; (e) the subject plant or plant cell itself, under conditions in which the gene of interest is not expressed or (f) the subject plant or plant cell itself, under conditions in which it has not been exposed to a particular treatment such as, for example, a herbicide or combination of herbicides and/or other chemicals. In some instances, an appropriate control plant or control plant cell may have a different genotype from the subject plant or plant cell but may share the herbicide-sensitive characteristics of the starting material for the genetic alteration(s) which resulted in the subject plant or cell (see, e.g., Green, (1998) *Weed Technology* 12:474-477; Green and Ulrich, (1993) *Weed Science* 41:508-516. In other embodiments, the null segregant can be used as a control, as they are genetically identical to DP-073496-4 with the exception of the transgenic insert DNA.

Classification of herbicides (i.e., the grouping of herbicides into classes and subclasses) is well-known in the art and includes classifications by HRAC (Herbicide Resistance Action Committee) and WSSA (the Weed Science Society of America) (see also, Retzinger and Mallory-Smith, (1997) *Weed Technology* 11:384-393). An abbreviated version of the HRAC classification (with notes regarding the corresponding WSSA group) can be found in Table 1 of PCT International Patent Application No. PCT/US2010/058011 (herein incorporated by reference).

Herbicides can be classified by their mode of action and/or site of action and can also be classified by the time at which they are applied (e.g., preemergent or postemergent), by the method of application (e.g., foliar application or soil application) or by how they are taken up by or affect the plant. For example, thifensulfuron-methyl and tribenuron-methyl are applied to the foliage of a crop and are generally metabolized there, while rimsulfuron and chlorimuron-ethyl are generally taken up through both the roots and foliage of a plant. "Mode of action" generally refers to the metabolic or physiological process within the plant that the herbicide inhibits or otherwise impairs, whereas "site of action" generally refers to the physical location or biochemical site within the plant where the herbicide acts or directly interacts. Herbicides can be classified in various ways, including by mode of action and/or site of action.

Often, a herbicide-tolerance gene that confers tolerance to a particular herbicide or other chemical on a plant expressing it will also confer tolerance to other herbicides or chemicals in the same class or subclass, for example, a class or subclass as set forth in the abbreviated version of the HRAC herbicide classification system (see Table 1; PCT International Patent Application No. PCT/US2010/058011, herein incorporated by reference).

In certain methods, glyphosate, alone or in combination with another herbicide of interest, can be applied to the *Brassica* plants or their area of cultivation. Non-limiting examples of glyphosate formulations are set forth in Table 1.

TABLE 1

Glyphosate formulations comparisons.

| Herbicide by Registered Trademark | Manufactuer | Salt | Active ingredient per gallon | Acid equivalent per gallon | Apply fl oz/ acre | Acid equivalent per acre |
|---|---|---|---|---|---|---|
| Roundup Original | Monsanto | Isopropylamine | 4 | 3 | 32 | 0.750 |
| Roundup Original II | Monsanto | Isopropylamine | 4 | 3 | 32 | 0.750 |
| Roundup Original MAX | Monsanto | Potassium | 5.5 | 4.5 | 22 | 0.773 |
| Roundup UltraMax | Monsanto | Isopropylamine | 5 | 3.68 | 26 | 0.748 |
| Roundup UltraMax II | Monsanto | Potassium | 5.5 | 4.5 | 22 | 0.773 |
| Roundup Weathermax | Monsanto | Potassium | 5.5 | 4.5 | 22 | 0.773 |
| Touchdown | Syngenta | Diammonium | 3.7 | 3 | 32 | 0.750 |
| Touchdown HiTech | Syngenta | Potassium | 6.16 | 5 | 20 | 0.781 |
| Touchdown Total | Syngenta | Potassium | 5.14 | 4.17 | 24 | 0.782 |
| Durango | Dow AgroSciences | Isopropylamine | 5.4 | 4 | 24 | 0.750 |
| Glyphomax | Dow AgroSciences | Isopropylamine | 4 | 3 | 32 | 0.750 |
| Glyphomax Plus | Dow AgroSciences | Isopropylamine | 4 | 3 | 32 | 0.750 |
| Glyphomax XRT | Dow AgroSciences | Isopropylamine | 4 | 3 | 32 | 0.750 |
| Gly Star Plus | Albaugh/Agri Star | Isopropylamine | 4 | 3 | 32 | 0.750 |
| Gly Star 5 | Albaugh/Agri Star | Isopropylamine | 5.4 | 4 | 24 | 0.750 |
| Gly Star Original | Albaugh/Agri Star | Isopropylamine | 4 | 3 | 32 | 0.750 |
| Gly-Flo | Micro Flo | Isopropylamine | 4 | 3 | 32 | 0.750 |
| Credit | Nufarm | Isopropylamine | 4 | 3 | 32 | 0.750 |
| Credit Extra | Nufarm | Isopropylamine | 4 | 3 | 32 | 0.750 |
| Credit Duo | Nufarm | Isopro. + monoamm. | 4 | 3 | 32 | 0.750 |
| Credit Duo Extra | Nufarm | Isopro. + monoamm. | 4 | 3 | 32 | 0.750 |
| Extra Credit 5 | Nufarm | Isopropylamine | 5 | 3.68 | 26 | 0.748 |
| Cornerstone | Agriliance | Isopropylamine | 4 | 3 | 32 | 0.750 |
| Cornerstone Plus | Agriliance | Isopropylamine | 4 | 3 | 32 | 0.750 |
| Glyfos | Cheminova | Isopropylamine | 4 | 3 | 32 | 0.750 |
| Glyfos X-TRA | Cheminova | Isopropylamine | 4 | 3 | 32 | 0.750 |
| Rattler | Helena | Isopropylamine | 4 | 3 | 32 | 0.750 |
| Rattler Plus | Helena | Isopropylamine | 4 | 3 | 32 | 0.750 |
| Mirage | UAP | Isopropylamine | 4 | 3 | 32 | 0.750 |
| Mirage Plus | UAP | Isopropylamine | 4 | 3 | 32 | 0.750 |
| Glyphosate 41% | Helm Agro USA | Isopropylamine | 4 | 3 | 32 | 0.750 |
| Buccaneer | Tenkoz | Isopropylamine | 4 | 3 | 32 | 0.750 |
| Buccaneer Plus | Tenkoz | Isopropylamine | 4 | 3 | 32 | 0.750 |
| Honcho | Monsanto | Isopropylamine | 4 | 3 | 32 | 0.750 |
| Honcho Plus | Monsanto | Isopropylamine | 4 | 3 | 32 | 0.750 |
| Gly-4 | Univ. Crop Prot. Alli | Isopropylamine | 4 | 3 | 32 | 0.750 |
| Gly-4 Plus | Univ. Corp Prot. Alli | Isopropylamme | 4 | 3 | 32 | 0.750 |
| ClearOut 41 | Chemical Products Tech. | Isopropylamine | 4 | 3 | 32 | 0.750 |
| ClearOut 41 Plus | Chemical Products Tech. | Isopropylamine | 4 | 3 | 32 | 0.750 |
| Spitfire | Control Solutions | Isopropylamine | 4 | 3 | 32 | 0.750 |
| Spitfire Plus | Control Solutions | Isopropylamine | 4 | 3 | 32 | 0.750 |
| Glyphosate 4 | FarmerSaver.com | Isopropylamine | 4 | 3 | 32 | 0.750 |
| FS Glyphosate Plus | Growmark | Isopropylamine | 4 | 3 | 32 | 0.750 |
| Glyphosate Original | Griffin, LLC | Isopropylamine | 4 | 3 | 32 | 0.750 |

Other suitable herbicides and agricultural chemicals are known in the art, such as, for example, those described in WO 2005/041654. Other herbicides also include bioherbicides such as *Alternaria destruens* Simmons, *Colletotrichum gloeosporiodes* (Penz.) Penz. and Sacc., *Drechsiera monoceras* (MTB-951), *Myrothecium verrucaria* (Albertini & Schweinitz) Ditmar: Fries, *Phytophthora palmivora* (Butl.) Butl. and *Puccinia thlaspeos* Schub. Combinations of various herbicides can result in a greater-than-additive (i.e., synergistic) effect on weeds and/or a less-than-additive effect (i.e., safening) on crops or other desirable plants. In certain instances, combinations of glyphosate with other herbicides having a similar spectrum of control but a different mode of action will be particularly advantageous for preventing the development of resistant weeds.

The methods further comprise applying to the crop and the weeds in a field a sufficient amount of at least one herbicide to which the crop seeds or plants are tolerant, such as, for example, glyphosate, a hydroxyphenylpyruvatedioxygenase inhibitor (e.g., mesotrione or sulcotrione), a phytoene desaturase inhibitor (e.g., diflufenican), a pigment synthesis inhibitor, sulfonamide, imidazolinone, bialaphos, phosphinothricin, azafenidin, butafenacil, sulfosate, glufosinate, triazolopyrimidine, pyrimidinyloxy(thio)benzoate or sulonylaminocarbonyltriazolinone, an acetyl Co-A carboxylase inhibitor such as quizalofop-P-ethyl, a synthetic auxin such as quinclorac, KIH-485 or a protox inhibitor to control the weeds without significantly damaging the crop plants.

Generally, the effective amount of herbicide applied to the field is sufficient to selectively control the weeds without significantly affecting the crop. "Weed" as used herein refers to a plant which is not desirable in a particular area. Conversely, a "crop plant" as used herein refers to a plant which is desired in a particular area, such as, for example, a *Brassica* plant. Thus, in some embodiments, a weed is a non-crop plant or a non-crop species. Weeds can be classified into two major groups: monocots and dicots.

Many plant species can be controlled (i.e., killed or damaged) by the herbicides described herein. Accordingly, the methods of the disclosure are useful in controlling these plant species where they are undesirable (i.e., where they are weeds). These plant species include crop plants as well as species commonly considered weeds, including but not limited to species such as: blackgrass (*Alopecurus myosuroides*), giant foxtail (*Setaria faberi*), large crabgrass (*Digitaria sanguinalis*), Surinam grass (*Brachiaria decumbens*), wild oat (*Avena fatua*), common cocklebur (*Xanthium pensylvanicum*), common lambsquarters (*Chenopodium album*), morning glory (*Ipomoea coccinea*), pigweed (*Amaranthus* spp.), velvetleaf (*Abufilion theophrasti*), common barnyardgrass (*Echinochloa crus-galli*), bermudagrass (*Cynodon dactylon*), downy brome (*Bromus tectorum*), goosegrass (*Eleusine indica*), green foxtail (*Setaria viridis*), Italian ryegrass (*Lolium multiflorum*), Johnsongrass (*Sorghum halepense*), lesser canarygrass (*Phalaris minor*), windgrass (*Apera spica-venti*), wooly cupgrass (*Erichloa villosa*), yellow nutsedge (*Cyperus esculentus*), common chickweed (*Stellaria media*), common ragweed (*Ambrosia artemisiifolia*), *Kochia scoparia*, horseweed (*Conyza canadensis*), rigid ryegrass (*Lolium rigidum*), goosegrass (*Eleucine indica*), hairy fleabane (*Conyza bonariensis*), buckhorn plantain (*Plantago lanceolata*), tropical spiderwort (*Commelina benghalensis*), field bindweed (*Convolvulus arvensis*), purple nutsedge (*Cyperus rotundus*), redvine (*Brunnichia ovata*), hemp sesbania (*Sesbania exaltata*), sicklepod (*Senna obtusifolia*), Texas blueweed (*Helianthus ciliaris*) and Devil's claws (*Proboscidea louisianica*). In other embodiments, the weed comprises an herbicide-resistant ryegrass, for example, a glyphosate resistant ryegrass, a paraquat resistant ryegrass, a ACCase-inhibitor resistant ryegrass and a non-selective herbicide resistant ryegrass. In some embodiments, the undesired plants are proximate the crop plants.

In some embodiments, a *Brassica* plant of the disclosure is not significantly damaged by treatment with a particular herbicide applied to that plant at a dose equivalent to a rate of at least 0.5, 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 110, 120, 150, 170, 200, 300, 400, 500, 600, 700, 800, 800, 1000, 2000, 3000, 4000, 5000, 5400 or more grams or ounces (1 ounce=29.57 ml) of active ingredient or commercial product or herbicide formulation per acre or per hectare, whereas an appropriate control plant is significantly damaged by the same treatment.

An effective amount of an ALS inhibitor herbicide comprises at least about 0.1, 1, 5, 10, 25, 50, 75, 100, 150, 200, 250, 300, 350, 400, 450, 500, 600, 700, 750, 800, 850, 900, 950, 1000, 2000, 3000, 4000, 5000 or more grams or ounces (1 ounce=29.57 ml) of active ingredient per hectare. In other embodiments, an effective amount of an ALS inhibitor comprises at least about 0.1-50, about 25-75, about 50-100, about 100-110, about 110-120, about 120-130, about 130-140, about 140-150, about 150-200, about 200-500, about 500-600, about 600-800, about 800-1000 or greater grams or ounces (1 ounce=29.57 ml) of active ingredient per hectare. Multiple ALS inhibitors can be applied at these levels.

An effective amount of a sulfonylurea comprises at least 0.1, 1, 5, 10, 25, 50, 75, 100, 150, 200, 250, 300, 350, 400, 450, 500, 600, 700, 800, 900, 1000, 5000 or more grams or ounces (1 ounce=29.57 ml) of active ingredient per hectare. In other embodiments, an effective amount of a sulfonylurea comprises at least about 0.1-50, about 25-75, about 50-100, about 100-110, about 110-120, about 120-130, about 130-140, about 140-150, about 150-160, about 160-170, about 170-180, about 190-200, about 200-250, about 250-300, about 300-350, about 350-400, about 400-450, about 450-500, about 500-550, about 550-600, about 600-650, about 650-700, about 700-800, about 800-900, about 900-1000, about 1000-2000 or more grams or ounces (1 ounce=29.57 ml) of active ingredient per hectare. Multiple sulfonylureas can be applied at this level.

An effective amount of a sulfonylaminocarbonyltriazolinones, triazolopyrimidines, pyrimidinyloxy(thio)benzoates, and imidazolinones can comprise at least about 0.1, 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1500, 1550, 1600, 1650, 1700, 1800, 1850, 1900, 1950, 2000, 2500, 3500, 4000, 4500, 5000 or greater grams or ounces (1 ounce=29.57 ml) active ingredient per hectare. In other embodiments, an effective amount of a sulfonyluminocarbonyltriazolines, triazolopyrimidines, pyrimidinyloxy(thio)benzoates or imidazolinones comprises at least about 0.1-50, about 25-75, about 50-100, about 100-110, about 110-120, about 120-130, about 130-140, about 140-150, about 150-160, about 160-170, about 170-180, about 190-200, about 200-250, about 250-300, about 300-350, about 350-400, about 400-450, about 450-500, about 500-550, about 550-600, about 600-650, about 650-700, about 700-800, about 800-900, about 900-1000, about 1000-2000 or more grams or ounces (1 ounce=29.57 ml) active ingredient per hectare.

Additional ranges of the effective amounts of herbicides can be found, for example, in various publications from University Extension services. See, for example, Bernards, et al., (2006) *Guide for Weed Management in Nebraska*;

Regher, et al., (2005) *Chemical Weed Control for Fields Crops, Pastures, Rangeland, and Noncropland*, Kansas State University Agricultural Extension Station and Corporate Extension Service; Zollinger, et al., (2006) *North Dakota Weed Control Guide*, North Dakota Extension Service and the Iowa State University Extension at each of which is herein incorporated by reference.

In some embodiments of the disclosure, glyphosate is applied to an area of cultivation and/or to at least one plant in an area of cultivation at rates between 8 and 32 ounces of acid equivalent per acre, or at rates between 10, 12, 14, 16, 18, 20, 22, 24, 26, 28 and 30 ounces of acid equivalent per acre at the lower end of the range of application and between 12, 14, 16, 18, 20, 22, 24, 26, 28, 30 and 32 ounces of acid equivalent per acre at the higher end of the range of application (1 ounce=29.57 ml). In other embodiments, glyphosate is applied at least at 1, 5, 10, 20, 30, 40, 50, 60, 70, 80, 90 or greater ounce of active ingredient per hectare (1 ounce=29.57 ml). In some embodiments of the disclosure, a sulfonylurea herbicide is applied to a field and/or to at least one plant in a field at rates between 0.04 and 1.0 ounces of active ingredient per acre, or at rates between 0.1, 0.2, 0.4, 0.6 and 0.8 ounces of active ingredient per acre at the lower end of the range of application and between 0.2, 0.4, 0.6, 0.8 and 1.0 ounces of active ingredient per acre at the higher end of the range of application. (1 ounce=29.57 ml). In some embodiments, as described herein, glyphosate treatment can be made at late stage canola development when needed for weed control.

As is known in the art, glyphosate herbicides as a class contain the same active ingredient, but the active ingredient is present as one of a number of different salts and/or formulations. However, herbicides known to inhibit ALS vary in their active ingredient as well as their chemical formulations. One of skill in the art is familiar with the determination of the amount of active ingredient and/or acid equivalent present in a particular volume and/or weight of herbicide preparation.

An ALS inhibitor herbicide is employed. Rates at which the ALS inhibitor herbicide is applied to the crop, crop part, seed or area of cultivation can be any of the rates disclosed herein. In specific embodiments, the rate for the ALS inhibitor herbicide is about 0.1 to about 5000 g ai/hectare, about 0.5 to about 300 g ai/hectare or about 1 to about 150 g ai/hectare.

Generally, a particular herbicide is applied to a particular field (and any plants growing in it) no more than 1, 2, 3, 4, 5, 6, 7 or 8 times a year, or no more than 1, 2, 3, 4 or 5 times per growing season.

By "treated with a combination of" or "applying a combination of herbicides to a crop, area of cultivation or field" it is intended that a particular field, crop or weed is treated with each of the herbicides and/or chemicals indicated to be part of the combination so that a desired effect is achieved, i.e., so that weeds are selectively controlled while the crop is not significantly damaged. In some embodiments, weeds which are susceptible to each of the herbicides exhibit damage from treatment with each of the herbicides which is additive or synergistic. The application of each herbicide and/or chemical may be simultaneous or the applications may be at different times, so long as the desired effect is achieved. Furthermore, the application can occur prior to the planting of the crop.

An "additive herbicidal composition" has an herbicidal activity that is about equal to the observed activities of the individual components. A "synergistic herbicidal combination" has an herbicidal activity higher than what can be expected based on the observed activities of the individual components when used alone. Accordingly, the presently disclosed subject matter provides a synergistic herbicide combination, wherein the degree of weed control of the mixture exceeds the sum of control of the individual herbicides. In some embodiments, the degree of weed control of the mixture exceeds the sum of control of the individual herbicides by any statistically significant amount including, for example, about 1% to 5%, about 5% to about 10%, about 10% to about 20%, about 20% to about 30%, about 30% to 40%, about 40% to about 50%, about 50% to about 60%, about 60% to about 70%, about 70% to about 80%, about 80% to about 90%, about 90% to about 100%, about 100% to 120% or greater. Further, a "synergistically effective amount" of an herbicide refers to the amount of one herbicide necessary to elicit a synergistic effect in another herbicide present in the herbicide composition. Thus, the term "synergist," and derivations thereof, refer to a substance that enhances the activity of an active ingredient (ai), i.e., a substance in a formulation from which a biological effect is obtained, for example, an herbicide.

For controlling undesired plants, glyphosate may be applied pre-emergence, post-emergence or pre- and post-emergence to the undesired plants or plant crops and/or the ALS inhibitor herbicide (i.e., the sulfonylurea herbicide) is applied pre-emergence, post-emergence or pre- and post-emergence to the undesired plants or plant crops. In other embodiments, the glyphosate and/or the ALS inhibitor herbicide (i.e., the sulfonylurea herbicide) are applied together or are applied separately. In yet other embodiments, the synergistic herbicide composition is applied, e.g., step (b) above, at least once prior to planting the crop(s) of interest, e.g., step (a) above.

Weeds that can be difficult to control with glyphosate alone in fields where a crop is grown (such as, for example, a *brassica* crop) include but are not limited to the following: horseweed (e.g., *Conyza canadensis*); rigid ryegrass (e.g., *Lolium rigidum*); goosegrass (e.g., *Eleusine indica*); Italian ryegrass (e.g., *Lolium multiflorum*); hairy fleabane (e.g., *Conyza bonariensis*); buckhorn plantain (e.g., *Plantago lanceolata*); common ragweed (e.g., *Ambrosia artemisifolia*); morning glory (e.g., *Ipomoea* spp.); waterhemp (e.g., *Amaranthus* spp.); field bindweed (e.g., *Convolvulus arvensis*); yellow nutsedge (e.g., *Cyperus esculentus*); common lambsquarters (e.g., *Chenopodium album*); wild buckwheat (e.g., *Polygonium convolvulus*); velvetleaf (e.g., *Abutilon theophrasti*); kochia (e.g., *Kochia scoparia*) and Asiatic dayflower (e.g., *Commelina* spp.). In areas where such weeds are found, *Brassica* plants tolerance to another herbicide are particularly useful in allowing the treatment of a field (and therefore any crop growing in the field) with combinations of herbicides that would cause unacceptable damage to crop plants that did not contain both of these polynucleotides. Plants of the disclosure that are tolerant to glyphosate and other herbicides such as, for example, sulfonylurea, imidazolinone, triazolopyrimidine, pyrimidinyl(thio)benzoate and/or sulfonylaminocarbonyltriazolinone herbicides in addition to being tolerant to at least one other herbicide with a different mode of action or site of action are particularly useful in situations where weeds are tolerant to at least two of the same herbicides to which the plants are tolerant. In this manner, plants of the disclosure make possible improved control of weeds that are tolerant to more than one herbicide.

Other commonly used treatments for weed control in fields where current commercial varieties of crops (including, for example, *Brassicas*) are grown include the sulfonylurea herbicide thifensulfuron-methyl (available commercially as Harmony GT®). However, one disadvantage of thifensulfuron-methyl is that the higher application rates required for consistent weed control often cause injury to a crop growing in the same field. *Brassica* plants comprising additional tolerance (in addition to glyphosate) can be treated with a combination of glyphosate and thifensulfuron-methyl, which has the advantage of using herbicides with different modes of action. Thus, weeds that are resistant to either herbicide alone are controlled by the combination of the two herbicides, and the improved GATT *Brassica* plants would not be significantly damaged by the treatment.

Other herbicides which are used for weed control in fields where current commercial varieties of crops (including, for example, *Brassicas*) are grown are the triazolopyrimidine herbicide cloransulam-methyl (available commercially as FirstRate®) and the imidazolinone herbicide imazaquin (available commercially as Sceptor®). When these herbicides are used individually they may provide only marginal control of weeds. However, commercial varieties of crops may be treated, for example, with a combination of glyphosate (e.g., Roundup® (glyphosate isopropylamine salt)), imazapyr (currently available commercially as Arsenal®), chlorimuron-ethyl (currently available commercially as Classic®), quizalofop-P-ethyl (currently available commercially as Assure II®) and fomesafen (currently available commercially as Flexstar®). This combination has the advantage of using herbicides with different modes of action. Thus, weeds that are tolerant to just one or several of these herbicides are controlled by the combination of the five herbicides. This combination provides an extremely broad spectrum of protection against the type of herbicide-tolerant weeds that might be expected to arise and spread under current weed control practices.

Fields containing the glyphosate-metabolizing tolerant *Brassica* plants with additional herbicide tolerance may also be treated, for example, with a combination of herbicides including glyphosate, rimsulfuron, and dicamba or mesotrione. This combination may be particularly useful in controlling weeds which have developed some tolerance to herbicides which inhibit ALS. Another combination of herbicides which may be particularly useful for weed control includes glyphosate and at least one of the following: metsulfuron-methyl (commercially available as Ally®), imazapyr (commercially available as Arsenal®), imazethapyr, imazaquin and sulfentrazone. It is understood that any of the combinations discussed above or elsewhere herein may also be used to treat areas in combination with any other herbicide or agricultural chemical.

Some commonly-used treatments for weed control in fields where current commercial crops (including, for example, *Brassica*) are grown include glyphosate (currently available commercially as Roundup®), rimsulfuron (currently available commercially as Resolve® or Matrix®), dicamba (commercially available as Clarity®), atrazine and mesotrione (commercially available as Callisto®). These herbicides are sometimes used individually due to poor crop tolerance to multiple herbicides. Unfortunately, when used individually, each of these herbicides has significant disadvantages. Particularly, the incidence of weeds that are tolerant to individual herbicides continues to increase, rendering glyphosate less effective than desired in some situations. Rimsulfuron provides better weed control at high doses which can cause injury to a crop, and alternatives such as dicamba are often more expensive than other commonly-used herbicides Some commonly-used treatments for weed control in fields where current commercial crops are grown include glyphosate (currently available commercially as Roundup®), chlorimuron-ethyl, tribenuron-methyl, rimsulfuron (currently available commercially as Resolve® or Matrix®), imazethapyr, imazapyr and imazaquin. Unfortunately, when used individually, each of these herbicides has significant disadvantages. Particularly, the incidence of weeds that are tolerant to individual herbicides continues to increase, rendering each individual herbicide less effective than desired in some situations. However, *Brassica* plants that are tolerant to glyphosate due to the expression of a glyphosate metabolizing enzyme such as GAT in combination with an additional herbicide tolerance trait can be treated with a combination of herbicides that would cause unacceptable damage to standard plant varieties, including combinations of herbicides that include at least one of those mentioned above.

Various combinations of herbicides, fungicides, and/or insecticides may be applied with glyphosate through to the harvest stage of canola or at least until the 10% flower stage. These include herbicides, but are not limited, to Lontrel® (active ingredient clopyralid), clethodim (currently available commercially as Select®, Centurion®), Equinox® (Tepraloxydim), Muster®, and Poast Ultra®. These fungicides include, but are not limited to, Lance® (boscalid), Proline®, Vertisan™, Headline®, Astound®, Tilt®/Propiconazole, Quadris®/Azoxystrobin, iprodiones (currently available commercially as Rovral®), Quash®, Serenade® Max™ (*Bacillus subtilis*), and Acapela™. These insecticides include, but are not limited to, Lorsban®, Decis®, Lambda-cyhalothrin (currently available commercially as Matador®), Dimethoate (currently available commercially as Lagon® or Cygon®), Cypermethrin (Ripcord®), Malathion, Monitor®, Permethrin (Pounce®), Sevin® XLR Plus, Coragen®, and Benevia®.

An herbicide may be formulated and applied to an area of interest such as, for example, a field or area of cultivation, in any suitable manner. An herbicide may be applied to a field in any form, such as, for example, in a liquid spray or as solid powder or granules. In specific embodiments, the herbicide or combination of herbicides that are employed in the methods comprise a tankmix or a premix. An herbicide may also be formulated, for example, as a "homogenous granule blend" produced using blends technology (see, e.g., U.S. Pat. No. 6,022,552, entitled "Uniform Mixtures of Pesticide Granules"). The blends technology of U.S. Pat. No. 6,022,552 produces a nonsegregating blend (i.e., a "homogenous granule blend") of formulated crop protection chemicals in a dry granule form that enables delivery of customized mixtures designed to solve specific problems. A homogenous granule blend can be shipped, handled, subsampled and applied in the same manner as traditional premix products where multiple active ingredients are formulated into the same granule.

Any herbicide formulation applied over the GATT *Brassica* plant can be prepared as a "tank-mix" composition. In such embodiments, each ingredient or a combination of ingredients can be stored separately from one another. The ingredients can then be mixed with one another prior to application. Typically, such mixing occurs shortly before application. In a tank-mix process, each ingredient, before mixing, typically is present in water or a suitable organic solvent. For additional guidance regarding the art of formulation, see, Woods, "The Formulator's Toolbox—Product Forms for Modern Agriculture" *Pesticide Chemistry and Bioscience, The Food-Environment Challenge*, Brooks and Roberts, Eds., Proceedings of the 9th International Congress on Pesticide Chemistry, The Royal Society of Chemistry, Cambridge, 1999, pp. 120-133. See also, U.S. Pat. No. 3,235,361, Column 6, line 16 through Column 7, line 19 and Examples 10-41; U.S. Pat. No. 3,309,192, Column 5, line 43 through Column 7, line 62 and Examples 8, 12, 15, 39, 41, 52, 53, 58, 132, 138-140, 162-164, 166, 167 and 169-182; U.S. Pat. No. 2,891,855, Column 3, line 66 through Column 5, line 17 and Examples 1-4; Klingman, *Weed Control as a Science*, John Wiley and Sons, Inc., New York, 1961, pp 81-96 and Hance, et al., *Weed Control Handbook*, 8th Ed., Blackwell Scientific Publications, Oxford, 1989, each of which is incorporated herein by reference in their entirety.

The methods of the disclosure further allow for the development of herbicide combinations to be used with the *Brassica* plants. In such methods, the environmental conditions in an area of cultivation are evaluated. Environmental conditions that can be evaluated include, but are not limited to, ground and surface water pollution concerns, intended use of the crop, crop tolerance, soil residuals, weeds present in area of cultivation, soil texture, pH of soil, amount of organic matter in soil, application equipment and tillage practices. Upon the evaluation of the environmental conditions, an effective amount of a combination of herbicides can be applied to the crop, crop part, seed of the crop or area of cultivation.

The herbicide applied to the *Brassica* plants of the disclosure serves to prevent the initiation of growth of susceptible weeds and/or serve to cause damage to weeds that are growing in the area of interest. In some embodiments, the herbicide or herbicide mixture exert these effects on weeds affecting crops that are subsequently planted in the area of interest (i.e., field or area of cultivation). In the methods of the disclosure, the application of the herbicide combination need not occur at the same time. So long as the field in which the crop is planted contains detectable amounts of the first herbicide and the second herbicide is applied at some time during the period in which the crop is in the area of cultivation, the crop is considered to have been treated with a mixture of herbicides according to the disclosure. Thus, methods of the disclosure encompass applications of herbicide which are "preemergent," "postemergent," "preplant incorporation" and/or which involve seed treatment prior to planting.

"Preemergent" refers to an herbicide which is applied to an area of interest (e.g., a field or area of cultivation) before a plant emerges visibly from the soil. "Postemergent" refers to an herbicide which is applied to an area after a plant emerges visibly from the soil. In some instances, the terms "preemergent" and "postemergent" are used with reference to a weed in an area of interest, and in some instances these terms are used with reference to a crop plant in an area of interest. When used with reference to a weed, these terms may apply to only a particular type of weed or species of weed that is present or believed to be present in the area of interest. While any herbicide may be applied in a preemergent and/or postemergent treatment, some herbicides are known to be more effective in controlling a weed or weeds when applied either preemergence or postemergence. For example, rimsulfuron has both preemergence and postemergence activity, while other herbicides have predominately preemergence (metolachlor) or postemergence (glyphosate) activity. These properties of particular herbicides are known in the art and are readily determined by one of skill in the art. Further, one of skill in the art would readily be able to select appropriate herbicides and application times for use with the transgenic plants of the disclosure and/or on areas in which transgenic plants of the disclosure are to be planted. "Preplant incorporation" involves the incorporation of compounds into the soil prior to planting.

Thus, the disclosure provides improved methods of growing a crop and/or controlling weeds. The disclosure also provides methods of growing a crop and/or controlling weeds which are "no-till" or "low-till" (also referred to as "reduced tillage"). In such methods, the soil is not cultivated or is cultivated less frequently during the growing cycle in comparison to traditional methods; these methods can save costs that would otherwise be incurred due to additional cultivation, including labor and fuel costs.

The methods of the disclosure encompass the use of simultaneous and/or sequential applications of multiple classes of herbicides. In some embodiments, the methods of the disclosure involve treating a plant of the disclosure and/or an area of interest (e.g., a field or area of cultivation) and/or weed with just one herbicide or other chemical such as, for example, a glyphosate herbicide.

The time at which an herbicide is applied to an area of interest (and any plants therein) may be important in optimizing weed control. The time at which an herbicide is applied may be determined with reference to the size of plants and/or the stage of growth and/or development of plants in the area of interest, e.g., crop plants or weeds growing in the area. The stages of growth and/or development of plants are known in the art. Thus, for example, the time at which a herbicide or other chemical is applied to an area of interest in which plants are growing may be the time at which some or all of the plants in a particular area have reached at least a particular size and/or stage of growth and/or development, or the time at which some or all of the plants in a particular area have not yet reached a particular size and/or stage of growth and/or development.

Different chemicals such as herbicides have different "residual" effects, i.e., different amounts of time for which treatment with the chemical or herbicide continues to have an effect on plants growing in the treated area. Such effects may be desirable or undesirable, depending on the desired future purpose of the treated area (e.g., field or area of cultivation). Thus, a crop rotation scheme may be chosen based on residual effects from treatments that will be used for each crop and their effect on the crop that will subsequently be grown in the same area. One of skill in the art is familiar with techniques that can be used to evaluate the residual effect of an herbicide; for example, generally, glyphosate has very little or no soil residual activity, while herbicides that act to inhibit ALS vary in their residual activity levels. Residual activities for various herbicides are known in the art, and are also known to vary with various environmental factors such as, for example, soil moisture levels, temperature, pH and soil composition (texture and organic matter).

Moreover, the transgenic plants of the disclosure may provide improved tolerance to treatment with additional chemicals commonly used on crops in conjunction with herbicide treatments, such as safeners, adjuvants such as ammonium sulfonate and crop oil concentrate, and the like. The term "safener" refers to a substance that when added to an herbicide formulation eliminates or reduces the phytotoxic effects of the herbicide to certain crops. One of ordinary skill in the art would appreciate that the choice of safener depends, in part, on the crop plant of interest and the particular herbicide or combination of herbicides included in the synergistic herbicide composition. Exemplary safeners suitable for use with the presently disclosed herbicide compositions include, but are not limited to, those disclosed in U.S. Pat. Nos. 4,808,208; 5,502,025; 6,124,240 and US Patent Application Publication Numbers 2006/0148647; 2006/0030485; 2005/0233904; 2005/0049145; 2004/0224849; 2004/0224848; 2004/0224844; 2004/0157737; 2004/0018940; 2003/0171220; 2003/0130120; 2003/0078167, the disclosures of which are incorporated herein by reference in their entirety. The methods of the disclosure can involve the use of herbicides in combination with herbicide safeners such as benoxacor, BCS (1-bromo-4-[(chloromethyl) sulfonyl]benzene), cloquintocet-mexyl, cyometrinil, dichlormid, 2-(dichloromethyl)-2-methyl-1,3-dioxolane (MG 191), fenchlorazole-ethyl, fenclorim, flurazole, fluxofenim, furilazole, isoxadifen-ethyl, mefenpyr-diethyl, methoxyphenone ((4-methoxy-3-methylphenyl)(3-methylphenyl)-methanone), naphthalic anhydride (1,8-naphthalic anhydride) and oxabetrinil to increase crop safety. Antidotally effective amounts of the herbicide safeners can be applied at the same time as the compounds of this disclosure, or applied as seed treatments. Therefore an aspect of the present disclosure relates to the use of a mixture comprising glyphosate, at least one other herbicide and an antidotally effective amount of an herbicide safener.

As used herein, an "adjuvant" is any material added to a spray solution or formulation to modify the action of an agricultural chemical or the physical properties of the spray solution. See, for example, Green and Foy, (2003) "Adjuvants: Tools for Enhancing Herbicide Performance," in *Weed Biology and Management*, ed. Inderjit (Kluwer Academic Publishers, The Netherlands). Adjuvants can be categorized or subclassified as activators, acidifiers, buffers, additives, adherents, antiflocculants, antifoamers, defoamers, antifreezes, attractants, basic blends, chelating agents, cleaners, colorants or dyes, compatibility agents, cosolvents, couplers, crop oil concentrates, deposition agents, detergents, dispersants, drift control agents, emulsifiers, evaporation reducers, extenders, fertilizers, foam markers, formulants, inerts, humectants, methylated seed oils, high load COCs, polymers, modified vegetable oils, penetrators, repellants, petroleum oil concentrates, preservatives, rainfast agents, retention aids, solubilizers, surfactants, spreaders, stickers, spreader stickers, synergists, thickeners, translocation aids, uv protectants, vegetable oils, water conditioners and wetting agents.

In addition, the *brassica* tolerant plants of the disclosure may be treated with a mixture of herbicides, as well as, one or more other insecticides, fungicides, nematocides, bactericides, acaricides, growth regulators, chemosterilants, semiochemicals, repellents, attractants, pheromones, feeding stimulants or other biologically active compounds or entomopathogenic bacteria, virus or fungi to form a multi-component mixture giving an even broader spectrum of agricultural protection. Examples of such agricultural protectants which can be used in methods of the disclosure include: insecticides such as abamectin, acephate, acetamiprid, amidoflumet (S-1955), avermectin, azadirachtin, azinphos-methyl, bifenthrin, bifenazate, buprofezin, carbofuran, cartap, chlorfenapyr, chlorfluazuron, chlorpyrifos, chlorpyrifos-methyl, chromafenozide, clothianidin, cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, metaflumizone, metaldehyde, methamidophos, methidathion, methomyl, methoprene, methoxychlor, metofluthrin, monocrotophos, methoxyfenozide, nitenpyram, nithiazine, novaluron, noviflumuron (XDE-007), oxamyl, parathion, parathion-methyl, permethrin, phorate, phosalone, phosmet, phosphamidon, pirimicarb, profenofos, profluthrin, pymetrozine, pyrafluprole, pyrethrin, pyridalyl, pyriprole, pyriproxyfen, rotenone, ryanodine, spinosad, spirodiclofen, spiromesifen (BSN 2060), spirotetramat, sulprofos, tebufenozide, teflubenzuron, tefluthrin, terbufos, tetrachlorvinphos, thiacloprid, thiamethoxam, thiodicarb, thiosultap-sodium, tralomethrin, triazamate, trichlorfon and triflumuron; fungicides such as acibenzolar, aldimorph, amisulbrom, azaconazole, azoxystrobin, benalaxyl, benomyl, benthiavalicarb, benthiavalicarb-isopropyl, binomial, biphenyl, bitertanol, blasticidin-S, Bordeaux mixture (Tribasic copper sulfate), boscalid/nicobifen, bromuconazole, bupirimate, buthiobate, carboxin, carpropamid, captafol, captan, carbendazim, chloroneb, chlorothalonil, chlozolinate, clotrimazole, copper oxychloride, copper salts such as copper sulfate and copper hydroxide, cyazofamid, cyflunamid, cymoxanil, cyproconazole, cyprodinil, dichlofluanid, diclocymet, diclomezine, dicloran, diethofencarb, difenoconazole, dimethomorph, dimoxystrobin, diniconazole, diniconazole-M, dinocap, discostrobin, dithianon, dodemorph, dodine, econazole, etaconazole, edifenphos, epoxiconazole, ethaboxam, ethirimol, ethridiazole, famoxadone, fenamidone, fenarimol, fenbuconazole, fencaramid, fenfuram, fenhexamide, fenoxanil, fenpiclonil, fenpropidin, fenpropimorph, fentin acetate, fentin hydroxide, ferbam, ferfurazoate, ferimzone, fluazinam, fludioxonil, flumetover, fluopicolide, fluoxastrobin, fluquinconazole, fluquinconazole, flusilazole, flusulfamide, flutolanil, flutriafol, folpet, fosetyl-aluminum, fuberidazole, furalaxyl, furametapyr, hexaconazole, hymexazole, guazatine, imazalil, imibenconazole, iminoctadine, iodicarb, ipconazole, iprobenfos, iprodione, iprovalicarb, isoconazole, isoprothiolane, kasugamycin, kresoxim-methyl, mancozeb, mandipropamid, maneb, mapanipyrin, mefenoxam, mepronil, metalaxyl, metconazole, methasulfocarb, metiram, metominostrobin/fenominostrobin, mepanipyrim, metrafenone, miconazole, myclobutanil, neo-asozin (ferric methanearsonate), nuarimol, octhilinone, ofurace, orysastrobin, oxadixyl, oxolinic acid, oxpoconazole, oxycarboxin, paclobutrazol, penconazole, pencycuron, penthiopyrad, perfurazoate, phosphonic acid, phthalide, picobenzamid, picoxystrobin, polyoxin, probenazole, prochloraz, procymidone, propamocarb, propamocarb-hydrochloride, propiconazole, propineb, proquinazid, prothioconazole, pyraclostrobin, pryazophos, pyrifenox, pyrimethanil, pyrifenox, pyrolnitrine, pyroquilon, quinconazole, quinoxyfen, quintozene, silthiofam, simeconazole, spiroxamine, streptomycin, sulfur, tebuconazole, techrazene, tecloftalam, tecnazene, tetraconazole, thiabendazole, thifluzamide, thiophanate, thiophanate-methyl, thiram, tiadinil, tolclofos-methyl, tolyfluanid, triadimefon, triadimenol, triarimol, triazoxide, tridemorph, trimoprhamide tricyclazole, trifloxystrobin, triforine, triticonazole, uniconazole, validamycin, vinclozolin, zineb, ziram, and zoxamide; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad and biological agents including entomopathogenic bacteria, such as *Bacillus thuringiensis* subsp. *Aizawai, Bacillus thuringiensis* subsp. *Kurstaki*, and the encapsulated delta-endotoxins of

*Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV. The weight ratios of these various mixing partners to other compositions (e.g., herbicides) used in the methods of the disclosure typically are between 100:1 and 1:100, or between 30:1 and 1:30, between 10:1 and 1:10, or between 4:1 and 1:4.

Thus, methods of the disclosure employ an herbicide or herbicide combination and may further comprise the use of insecticides and/or fungicides, and/or other agricultural chemicals such as fertilizers. The use of such combined treatments of the disclosure can broaden the spectrum of activity against additional weed species and suppress the proliferation of any resistant biotypes.

Methods of the disclosure can further comprise the use of plant growth regulators such as aviglycine, N-(phenylmethyl)-1H-purin-6-amine, ethephon, epocholeone, gibberellic acid, gibberellin $A_4$ and $A_7$, harpin protein, mepiquat chloride, prohexadione calcium, prohydrojasmon, sodium nitrophenolate and trinexapac-methyl and plant growth modifying organisms such as *Bacillus cereus* strain BP01.

The methods described herein also provide a means of minimizing adverse agronomic impact as a result of late stage weed development. Controlling weeds that grow during late stage canola development may result in less stover, less biological matter, and better farming harvest operations which ultimately results in a positive agronomic impact for the grower. Diseases that may be increased by weed growth in the field during late stage canola growth include, but are not limited to, blackleg, fusarium wilt, and sclerotinia. By controlling weed growth at late stage canola development, canola diseases may be controlled better. Therefore, glyphosate treatment at late stage canola development may provide a means to better controlling canola disease.

Canola Growth Stages

A growth stage scale called the BBCH demical system may be used to classify the different stages of canola growth (Meler, U ed), Growth Stages of mono- and dicotyledonous plants, 2. Edition (2001) (Federal Biological Research Centre for Agriculture and Forestry, Berlin and Braunschweig; Lancashire, P. D., H. Bleiholder, P. Langeluddecke, R. T. Van Den Boom, E. Weber and A. Witzen-Berger, An uniformdecimal code for growth stages of crops and weeds. *Ann. appl. Biol.* 119, 561-601). The BBCH scale for canola describes nine principal growth stages for canola and corresponding codes and descriptions. The scale is divided into germination, leaf development, formation of side shoots, stem elongation, infloresence emergence, flowering, development of fruit, ripening, and senescence principal growth stages and further divided into subgroups. The BBCH growth stages are set forth in Table 2.

TABLE 2

Phenological growth stages and BBCH-identification keys of canola.

| Principal Growth Stage | Code | Description |
|---|---|---|
| 0: Germination | 00 | Dry seed |
| | 01 | Beginning of seed imbibition |
| | 03 | Seed imbibition complete |
| | 05 | Radicle emerged from seed |
| | 07 | Hypocotyl with cotyledons emerged from seed |
| | 08 | Hypocotyl with cotyledons growing towards soil surface |
| | 09 | Emergence: cotyledons emerge through soil surface |
| 1: Leaf development[1] | 10 | Cotyledons completely unfolded |
| | 11 | First leaf unfolded |
| | 12 | 2 leaves unfolded |
| | 13 | 3 leaves unfolded |
| | 1. | Stages continuous till . . . |
| | 19 | 9 or more leaves unfolded |
| 2: Formation of side shoots | 20 | No side shoots |
| | 21 | Beginning of side shoot development: first side shoot detectable |
| | 22 | 2 side shoots detectable |
| | 23 | 3 side shoots detectable |
| | 2. | Stages continuous till . . . |
| | 29 | End of side shoot development: 9 or more side shoots detectable |
| 3: Stem elongation[2] | 30 | Beginning of stem elongation: no internodes (“rosette”) |
| | 31 | 1 visibly extended internode |
| | 32 | 2 visibly extended internodes |
| | 33 | 3 visibly extended internodes |
| | 3. | Stages continuous till . . . |
| | 39 | 9 or more visibly extended internodes |
| 5: Inflorescence emergence | 50 | Flower buds present, still enclosed by leaves |
| | 51 | Flower buds visible from above (“green bud”) |
| | 52 | Flower buds free, level with the youngest leaves |
| | 53 | Flower buds raised above the youngest leaves |
| | 55 | Individual flower buds (main inflorescence) visible but still closed |
| | 57 | Individual flower buds (secondary inflorescences) visible but still closed |
| | 59 | First petals visible, flower buds still closed (“yellow bud”) |
| 6: Flowering | 60 | First flowers open |
| | 61 | 10% of flowers on main raceme open, main raceme elongating |
| | 62 | 20% of flowers on main raceme open |
| | 63 | 30% of flowers on main raceme open |
| | 64 | 40% of flowers on main raceme open |

TABLE 2-continued Phenological growth stages and BBCH-identification keys of canola.

| Principal Growth Stage | Code | Description |
|---|---|---|
| | 65 | Full flowering: 50% flowers on main raceme open, older petals falling |
| | 67 | Flowering declining: majority of petals fallen |
| | 69 | End of flowering |
| 7: Development of fruit | 71 | 10% of pods have reached final size |
| | 72 | 20% of pods have reached final size |
| | 73 | 30% of pods have reached final size |
| | 74 | 40% of pods have reached final size |
| | 75 | 50% of pods have reached final size |
| | 76 | 60% of pods have reached final size |
| | 77 | 70% of pods have reached final size |
| | 78 | 80% of pods have reached final size |
| | 79 | Nearly all pods have reached final size |
| 8: Ripening | 80 | Beginning of ripening: seed green, filling pod cavity |
| | 81 | 10% of pods ripe, seeds dark and hard |
| | 82 | 20% of pods ripe, seeds dark and hard |
| | 83 | 30% of pods ripe, seeds dark and hard |
| | 84 | 40% of pods ripe, seeds dark and hard |
| | 85 | 50% of pods ripe, seeds dark and hard |
| | 86 | 60% of pods ripe, seeds dark and hard |
| | 87 | 70% of pods ripe, seeds dark and hard |
| | 88 | 80% of pods ripe, seeds dark and hard |
| | 89 | Fully ripe: nearly all pods ripe, seeds dark and hard |
| 9: Senescence | 97 | Plant dead and dry |
| | 99 | Harvested product |

[1]= stem elongation may occur earlier than stage 19; in this case continue with stage 20.
[2]= visibly extended inernode n develops between leaf n and leaf n + 1

Embodiments of the present disclosure are further defined in the following Examples. It should be understood that these Examples are given by way of illustration only. From the above discussion and these Examples, one skilled in the art can ascertain the essential characteristics of this disclosure, and without departing from the spirit and scope thereof, can make various changes and modifications of the embodiments of the disclosure to adapt it to various usages and conditions. Thus, various modifications of the embodiments of the disclosure, in addition to those shown and described herein, will be apparent to those skilled in the art from the foregoing description. Such modifications are also intended to fall within the scope of the appended claims.

EXPERIMENTAL

Example 1. Herbicide Efficacy Trials for GAT Events for Determination of Yield

Field trials were split plot designed with glyphosate treatments as the main factor and entries as the subplot. The split-plot design was used since more than one glyphosate treatment in each location was evaluated, where a different treatment to an individual plot was applied. In split-plot, the levels of the main-plot factor (glyphosate treatments) and the sub-plot factors (individual event entries) within the main-plots were randomized.

The following treatments with glyphosate were used as detailed below at different growth stages. In these tests, 1X glyphosate treatment was at 675 g ae/ha, 2X glyphosate treatment was at 1350 g ae/ha, 3X glyphosate treatment was at 2025 g ae/ha and 4X glyphosate treatment was at 2700 g ae/ha as active ingredient of glyphosate. All treatments were applied using a mechanical sprayer. For example, in Treatment 1 below, "2X cotyledon" describes a treatment of 1350 g ae/ha of glyphosate at the cotyledon growth stage. Various treatments were tested over a two year period and are described below.

Treatments Tested in Year 1:
1. 2X cotyledon
2. 2X 3-5 leaf stage
3. 2X cot+2X 3-5 leaf stage
4. 2X cot+2X bolting BBCH55
5. 4X cotyledon
6. 4X 3-5 leaf stage Treatments Tested in Year 2:
1. 1X cotyledon+1X 3-5 leaf stage
2. 2X cotyledon+2X 3-5 leaf stage
3. 1X cotyledon+1X green bud BBCH51
4. 2X cotyledon+2X green bud BBCH51
5. 1X cotyledon+1X 10% flower BBCH61
6. 2X cotyledon+2X 10% flower BBCH61

To reduce the growth of weeds in the control plots, conventional herbicides or mechanical pulling of weeds were used as needed. There was no glyphosate applied to the control plots and was used as the control/base to which other glyphosate treatments were compared. The control plots may have had one or more weeds present during the growing season. Control is based on conventional herbicides that are registered for use in all canola.

Plots were considered desiccated when 60-70% of the seed had turned from green to black colour. Combining occurred 5-14 days after desiccation depending on the weather conditions. Each plot was harvested individually. Moisture and weight were recorded directly on the combine. Yield was determined for the GAT1 event.

Various locations were used in the test. Trials were evaluated across 10 locations in both Year 1 and Year 2. Locations included several sites in the short, mid, and long season zones across both years.

The event that was tested was canola event DP-73496-4 (GAT1) (PCT International Patent Application No. PCT/US2010/058011, incorporated by reference).

Example 2. Herbicide Efficacy Trials for GAT Events for Determination of Chlorosis Field trials were split plot designed with glyphosate treatments as the main factor and entries as the subplot. Entries were randomized within the split factor, and the split was randomized within the replicate.

The following treatments with glyphosate were used as detailed below at different growth stages. In these tests, 1X glyphosate treatment was 675 g ae/ha, 2X glyphosate treatment was 1350 g ae/ha, 3X glyphosate treatment was 2025 g ae/ha and 4X glyphosate treatment was 2700 g ae/ha. All treatments were applied using a mechanical sprayer. For example, in Treatment 1 below, "2X cotyledon" describes a treatment of 1350 g ae/ha of glyphosate at the cotyledon growth stage. Various treatments were tested over a two year period and are described below.

Treatments Tested in Year 1:
1. 2X cotyledon
2. 2X 3-5 leaf stage
3. 2X cot+2X 3-5 leaf stage
4. 2X cot+2X bolting BBCH55
5. 4X cotyledon
6. 4X 3-5 leaf stage Treatments Tested in Year 2:
1. 1X cotyledon+1X 3-5 leaf stage
2. 2X cotyledon+2X 3-5 leaf stage
3. 1X cotyledon+1X green bud BBCH51
4. 2X cotyledon+2X green bud BBCH51
5. 1X cotyledon+1X 10% flower BBCH61
6. 2X cotyledon+2X 10% flower BBCH61

Control treatments were used as comparisions (see Example 1).

The event that was tested was canola transformation event DP-73496-4 (GATT).

Percent chlorosis was determined. Visual rating of chlorosis on plants was taken during the period indicated (i.e. 3-5 days) after spray application. Yellowing of the apical meristem, newest leaves or older leaves indicated herbicide-induced chlorotic injury. 100%=all tissue is yellow, 0%=no signs of yellowing tissue.

Indicators for chlorosis were as follows:
HERBICIDE INJURY—CHLOROSIS (HINCL)
3-5 DAY (HINCL_5) describes the visual rating of chlorosis 5 days after treatment.
7-10 DAY (HINCL_10) describes the visual rating of chlorosis 10 days after treatment.
14-21 DAY (HINCL_21) describes the visual rating of chlorosis 21 days after treatment.
21-30 DAY (HINCL_30) describes the visual rating of chlorosis 30 days after treatment.
Rated 0 to 100%

Example 3. Herbicide Efficacy Trials for GAT Events for Determination of Necrosis Field trials were split plot designed with glyphosate treatments as the main factor and entries as the subplot. Entries were randomized within the split factor, and the split was randomized within the replicate.

The following treatments with glyphosate were used as detailed below at different growth stages. In these tests, 1X glyphosate treatment was 675 g ae/ha, 2X glyphosate treatment was 1350 g ae/ha, 3X glyphosate treatment was 2025 g ae/ha and 4X glyphosate treatment was 2700 g ae/ha. All treatments were applied using a mechanical sprayer. For example, in Treatment 1 below, "2X cotyledon" describes a treatment of 1350 g ae/ha of glyphosate at the cotyledon growth stage. Various treatments were tested over a two year period and are described below.

Treatments Tested in Year 1:
1. 2X cotyledon
2. 2X 3-5 leaf stage
3. 2X cot+2X 3-5 leaf stage
4. 2X cot+2X bolting BBCH55
5. 4X cotyledon
6. 4X 3-5 leaf stage Treatments Tested in Year 2:
1. 1X cotyledon+1X 3-5 leaf stage
2. 2X cotyledon+2X 3-5 leaf stage
3. 1X cotyledon+1X green bud BBCH51
4. 2X cotyledon+2X green bud BBCH51
5. 1X cotyledon+1X 10% flower BBCH61
6. 2X cotyledon+2X 10% flower BBCH61

Conventional chemical treatments were used as one of the controls (see Example 1).

Percentage necrosis was determined as follows. Visual rating of dead tissue on plants was taken during the period indicated (i.e. 3-5 days) after spray application. Brown or yellowing spots are early signs of damage. Dry brown tissue is advanced damage. 100% completely dead plant, 0%=no signs of dying tissue.

Indicators for necrosis were as follows:
HERBICIDE CROP RESPONSE—NECROSIS (HINNE)
3-5 DAY (HINNE_5) describes a visual rating of necrosis 5 days after herbicide treatment.
7-10 DAY (HINNE_10) describes a visual rating of necrosis 10 days after herbicide treatment.
14-21 DAY (HINNE_21) describes a visual rating of necrosis 21 days after herbicide treatment.
21-30 DAY (HINNE_30) describes a visual rating of necrosis 30 days after herbicide treatment.
Rated 0 to 100%

The event that was tested was canola transformation event DP-73496-4 (GAT1).

Example 4. Late Stage Application of Glyphosate on GAT Events

Late stage glyphosate applications are applications of glyphosate at later growth stages than on the glyphosate label. One of the purposes of evaluating the GAT1 canola crop response beyond the current glyphosate label growth stage was to test whether any crop response observed for the herbicide treatments did not significantly impact yield compared to the control treatment. In Year 1, the expanded window application of glyphosate was 2X cot+2X bolting BBCH55; a 2X treatment during the cotyledon stage and an additional 2X treatment during the plant growth stage where individual flower buds (main inflorescence) are visible but are still closed. In Year 2, 1X cotyledon, 1X green bud BBCH51; 2X cotyledon, 2X green bud BBCH51; 1X cotyledon, 1X 10% flower BBCH61; and 2X cotyledon, 2X 10% flower BBCH61 expanded window treatments were included.

Example 5. Comparison of GAT 1 to Control Treatments and Checks

Crop response was similar across 3 hybrid background in Year 1 2X Cot and 2X Bolting BBCH55 expanded window treatment. All three hybrids evaluated in one location showed 1% chlorosis. One hybrid background had 3% chlorosis in a second location and there was no crop response to this late glyphosate application treatment in the remaining eight locations. Full recovery of this low level transient chlorosis was observed 10 days after glyphosate application and yield was not significantly different compared to the control treatment. Four GAT-expressing canola backgrounds evaluated in extended window glyphosate treatments in Year 2 did not have any crop response. Treatments included split applications 1X Cot and 1X BBCH51 (green bud stage); 1X Cot and 1X BBCH61 (10% flower stage) across four backgrounds which did not result in yield reduction as compared to the control treatment. Additionally, the other two late split application treatments were 2X glyphosate (1350 g ae/ha) conducted at the same growth stages which did not result in yield reduction as compared to the control treatment. Compared to the controls, GAT1 did not show a reduction in yield at X treatment.

Example 6. Comparison of GAT 2 to ControlTreatments and Checks

Figure 2:
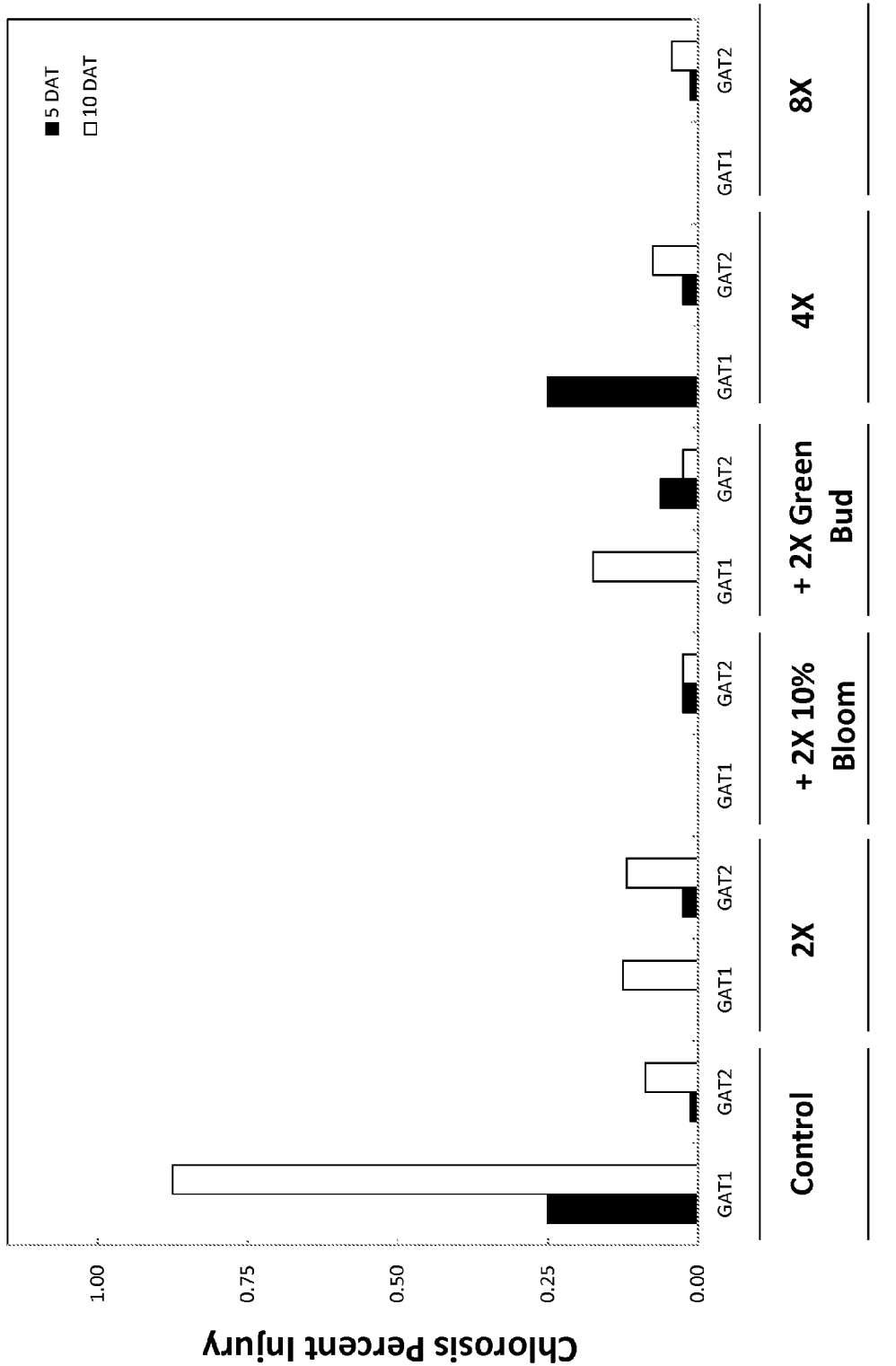
FIG. 2 shows herbicide efficacy data for eight transgenic lines at six different glyphosate treatments. The x axis indicates treatment type. The y axis indicates chlorosis percent injury.
Figure 3:
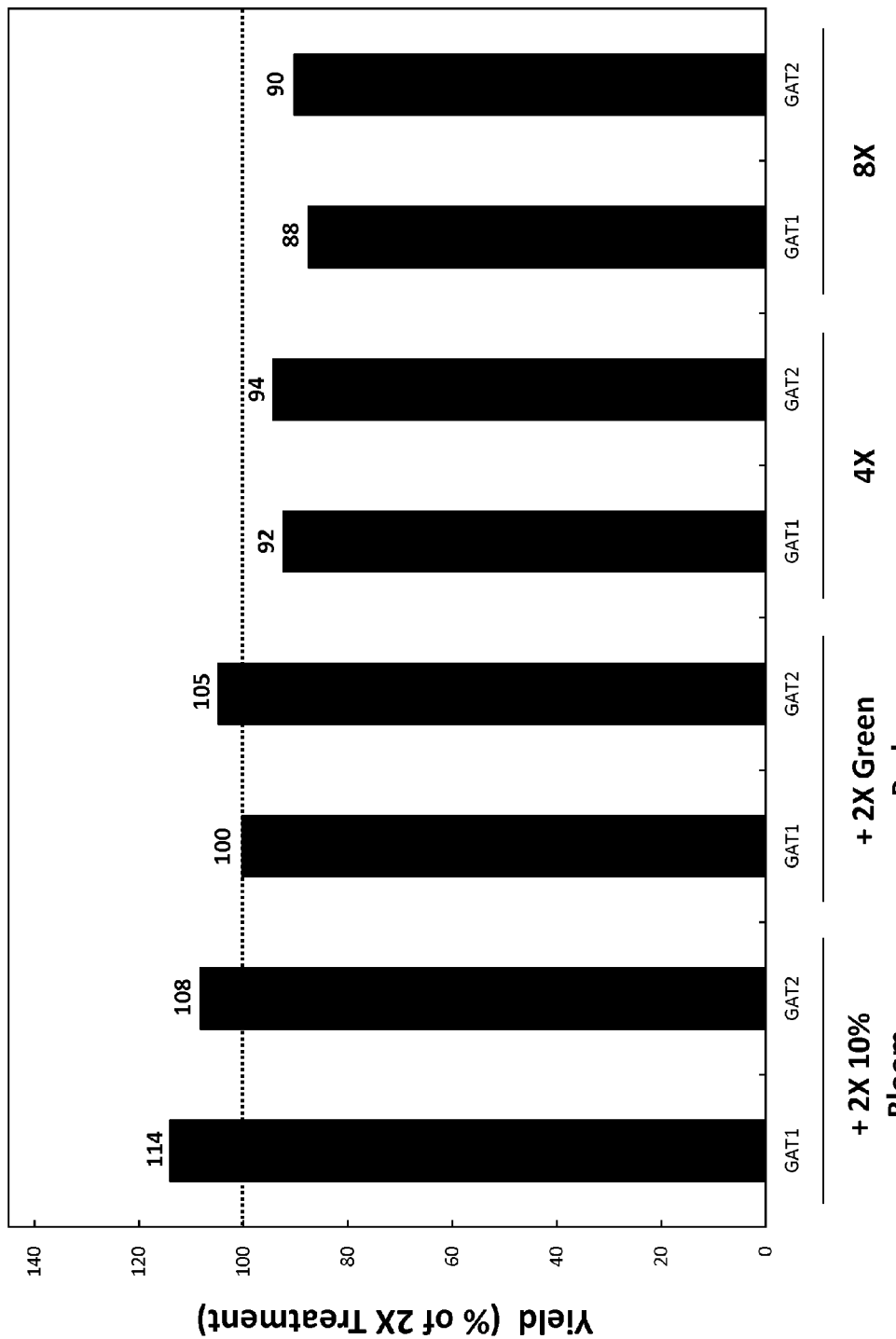
FIG. 3 shows herbicide efficacy data for eight transgenic lines at four glyphosate treatments. The y axis indicates percentage of yield relative to the 2X treatment at the 3 to 5 leaf stage. The x axis indicates the different treatment type.

GAT2 events were subjected to herbicide efficacy trials along with the GAT1 as diagonal check in 9 different locations. The herbicide efficacy trials consisted of 6 treatments that included: a control with no glyphosate, 2X, 4X or 8X glyphosate administered at the 3-5 leaf stage (1X=675 g ae/ha), a 2X administered during the 3-5 leaf stage and during the green bud stage (+2X Green Bud), and a 2X administered during the 3-5 leaf stage and during 10% bloom (+2X 10% Bloom). Herbicide-induced necrosis and chlorosis injury was recorded at leaf stages 5, 10, 21 and 30 DAT (days after treatment). No injury was observed beyond 10 DAT, and herbicide-induced necrotic injury was minimally observed, even at 8X spray rates (FIG. 1). Negligible chlorotic injury was observed in the both GAT1 and GAT2 events tested, even at 8X spray rates, and during green bud, and 10% bloom (FIG. 2). Yield from different treatments was expressed as a percent to the 2X treatment at the 3 to 5 leaf stage. The exposure of 2X application of glyphosate at the 3-5 leaf stage, and during the green bud or 10% bloom stage led to no appreciable differences in yield compared to the respective 2X treatment in both GATT and GAT2 (FIG. 3). The application of 4X glyphosate at the 3-5 leaf stage led to a 6 to 8% decrease in yield compared to the 2X treatment, and at the 8X rate, yield decreased from 10 to 12% in treated events compared to the 2X treatment (FIG. 3).

Example 7. Glyphosate Application Beyond the 10% Bloom Stage

Extended window treatments may include 4X glyphosate applications when 20% of the flowers are open on the main raceme (BBCH62) and 2X glyphosate applications when 30% of the flowers are open on the main raceme (BBCH63). These treatments may allow growers to have effective weed control on tough to control weeds with higher glyphosate application rates and extended weed control into the early flowering growth stages. Glyphosate application at these stages may result in superior weed control and therefore higher yields at maturity thus resulting in economic benefits for canola growers All publications and patent applications mentioned in the specification are indicative of the level of those skilled in the art to which this disclosure pertains. All publications and patent applications are herein incorporated by reference to the same extent as if each individual publication or patent application was specifically and individually indicated to be incorporated by reference.

Although the foregoing disclosure has been described in some detail by way of illustration and example for purposes of clarity of understanding, it will be obvious that certain changes and modifications may be practiced within the scope of the appended claims.

That which is claimed:

1. A method of improving weed control in a field containing herbicide tolerant *brassica* species, the method comprising
   (a) applying a glyphosate treatment comprising an effective amount of glyphosate over a population of glyphosate tolerant *brassica* plants, wherein a substantial portion of the glyphosate tolerant *brassica* plants are at about the flowering stage exhibiting at least 10% open flowers and wherein a substantial portion of open flowers do not show significant discoloration post-glyphosate treatment and further wherein the glyphosate tolerant *brassica* plants comprise a DP-073496-4 event that expresses a glyphosate acetyl transferase (GAT) enzyme; and
   (b) improving weed control in the field.

2. The method of claim 1, wherein the glyphosate tolerant *brassica* plants express a glyphosate acetyl transferase (GAT) enzyme in combination with an enzyme that provides tolerance to glufosinate herbicide.

3. The method of claim 1, wherein the open flowers do not show significant discoloration within 5 days post-glyphosate treatment.

4. The method of claim 1 wherein the glyphosate treatment comprises in a single application about 675, 1350, 2025, or 2700 g acid equivalent/hectare of glyphosate as the active ingredient.

5. The method of claim 1, wherein the glyphosate treatment comprises up to about 5400 g acid equivalent/hectare of glyphosate as the active ingredient in one or more cumulative applications.

6. A method of improving weed control in a field containing glyphosate-tolerant *brassica* species, the method comprising:
   (a) applying one or more glyphosate treatments comprising an effective amount of glyphosate over a population of glyphosate tolerant *brassica* plants that comprise a DP-073496-4 event, wherein a substantial portion of the *brassica* plants are at a stage that is beyond the 6-leaf stage and up to 10% open flowers; and
   (b) obtaining *brassica* seeds from the *brassica* plants, wherein a substantial portion of pods are not aborted post-glyphosate treatment.

7. A method of preventing yield loss or yield penalty at harvest of *brassica* plants, the method comprising:
   (a) applying a first glyphosate treatment comprising an effective amount of glyphosate over a population of glyphosate tolerant *brassica* plants that comprise a DP-073496-4 event;
   (b) applying one or more additional glyphosate treatments comprising an effective amount of glyphosate over the population of glyphosate tolerant *brassica* plants that comprise a DP-073496-4 event, wherein a substantial portion of the *brassica* plants are at a stage that is beyond the 6-leaf stage and up to 10% open flowers; and
   (c) obtaining *brassica* seeds from the *brassica* plants, wherein the yield loss is minimized due to a substantial reduction in discoloration or pod abortion after one or more late-stage applications of glyphosate.

8. A method of weed control in a field, the method comprising:
   (a) planting a population of glyphosate tolerant *brassica* plants in the field, wherein the *brassica* plants comprise a DP-073496-4 event that expresses a glyphosate acetyl transferase enzyme; and
   (b) applying a glyphosate treatment to the *brassica* field, wherein a substantial portion of the *brassica* plants are at a stage that is beyond the 6-leaf stage and up to 10% open flowers and thereby substantially reducing the growth of weeds in the *brassica* field.

9. A method of late season weed control in a field having a *brassica* crop without adversely affecting the yield, the method comprising:
   (a) planting a population of *brassica* plants that are tolerant to glyphosate wherein the plants comprise a DP-073496-4 event that expresses a glyphosate metabolizing enzyme such that the expression of the enzyme results in effective glyphosate tolerance;
   (b) applying an effective amount of glyphosate to the *brassica* plants wherein a substantial portion of the *brassica* plants are beyond the 6-leaf stage and up to 10% open flowers and wherein the glyphosate application does not result in significant chlorosis; and
   (c) controlling the growth of weeds in the field and wherein the *brassica* crop yield is not reduced by more than 5% compared to control *brassica* plants not expressing the glyphosate metabolizing enzyme.

10. The method of claim 9, wherein the glyphosate treatment comprises 1350-2700 g ae/hectare of glyphosate and a substantial portion of the *brassica* plants are at about 10% flower stage.

11. The method of claim 9, wherein the glyphosate application further comprises a disease control agent selected from the group consisting of insecticides, fungicides, and pesticides.

12. The method of claim 9, wherein the glyphosate application further comprises a late season nutrient application.

13. The method of claim 9, wherein the glyphosate is premixed with a disease control agent selected from the group consisting of insecticides, fungicides, and pesticides.

* * * * *